United States Patent
Kotlov et al.

(10) Patent No.: US 11,568,959 B2
(45) Date of Patent: Jan. 31, 2023

(54) TUMOR MICROENVIRONMENT-BASED METHODS FOR ASSESSING CAR-T AND OTHER IMMUNOTHERAPIES

(71) Applicant: BostonGene Corporation, Waltham, MA (US)

(72) Inventors: Nikita Kotlov, Moscow (RU); Georgy Sagaradze, Moscow (RU); Alexander Bagaev, Moscow (RU); Grigorii Nos, Moscow (RU); Lev Bedniagin, St. Petersburg (RU); Dmitry Kravchenko, Moscow (RU); Anna Gribkova, Moscow (RU)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 17/368,674

(22) Filed: Jul. 6, 2021

(65) Prior Publication Data

US 2022/0005551 A1    Jan. 6, 2022

Related U.S. Application Data

(60) Provisional application No. 63/128,426, filed on Dec. 21, 2020, provisional application No. 63/048,378, filed on Jul. 6, 2020.

(51) Int. Cl.
| | |
|---|---|
| *G16B 40/00* | (2019.01) |
| *A61P 35/00* | (2006.01) |
| *G16B 30/00* | (2019.01) |
| *A61K 35/17* | (2015.01) |
| *C07K 16/28* | (2006.01) |

(52) U.S. Cl.
CPC ............. *G16B 40/00* (2019.02); *A61K 35/17* (2013.01); *A61P 35/00* (2018.01); *C07K 16/2887* (2013.01); *G16B 30/00* (2019.02); *C07K 2317/24* (2013.01)

(58) Field of Classification Search
CPC ...................................................... G16B 40/00
USPC ...................................................... 424/133.1
See application file for complete search history.

(56) References Cited

U.S. PATENT DOCUMENTS

2019/0314410 A1    10/2019    Rossi et al.

OTHER PUBLICATIONS

Tockman et al (Cancer Res., 1992, 52:2711s-2718s).*
Chavez et al (Best Practice & Research Clinical Haematology, 2018, 31: 135-146).*
Cohen et al (Immunotherapy, 2017, 9(2): 183-196).*
International Search Report and Written Opinion for International Application No. PCT/US2021/040469 dated Nov. 9, 2021.
Cerchietti et al., Microenvironmental signatures reveal biological subtypes of diffuse large B-cell lymphoma (DLBCL) distinct from tumor cell molecular profiling. Blood. American Society of Hematology. Nov. 13, 2019. 134:656.
Kondou et al., Classification of tumor microenvironment immune types based on immune response-associated gene expression. International journal of oncology. Jan. 1, 2019;54(1):219-28.
Opinto et al., The tumor microenvironment of DLBCL in the computational era. Frontiers in oncology. Mar. 31, 2020;10:351.
Román-Pérez et al., Gene expression in extratumoral microenvironment predicts clinical outcome in breast cancer patients. Breast Cancer Research. Apr. 2012;14(2):1-2.

* cited by examiner

*Primary Examiner* — Sean E Aeder
(74) *Attorney, Agent, or Firm* — Wolf, Greenfield & Sacks, P.C.

(57) ABSTRACT

Aspects of the disclosure relate to methods for determining whether or a subject is likely to respond to certain adoptive cell therapies (e.g., chimeric antigen receptor (CAR) T-cell therapy, etc.). In some embodiments, the methods comprise the steps of identifying a subject as having a tumor microenvironment (TME) type based upon a molecular-functional (MF) expression signature of the subject, and determining whether or not the subject is likely to respond to a chimeric antigen receptor (CAR) T-cell therapy based upon the TME type. In some embodiments, the methods comprise determining the lymphoma microenvironment (LME) type of a lymphoma (e.g., Diffuse Large B cell lymphoma (DLBCL)) subject and identifying the subject's prognosis based upon the LME type determination.

4 Claims, 7 Drawing Sheets

TUMOR MICROENVIRONMENT-BASED METHODS FOR ASSESSING CAR-T AND OTHER IMMUNOTHERAPIES

RELATED APPLICATIONS

This Application claims the benefit under 35 U.S.C. 119(e) of the filing date of U.S. provisional Application Ser. No. 63/128,426, filed Dec. 21, 2020, and U.S. provisional Application Ser. No. 63/048,378, filed Jul. 6, 2020, the entire contents of each of which are incorporated herein by reference.

BACKGROUND

Adoptive cell transfer is a targeted immune cell therapy that often involves engineering a patient's immune cells to recognize and attack his or her tumor(s). Immune cells collected from a patient's blood can be genetically engineered to express receptors on the immune cell surface, which permits recognition by the immune cells of specific ligand proteins (e.g., antigens) expressed on a tumor cell surface. In vitro-expanded populations of these genetically engineered immune cells are infused back into the patient, the immune cells multiply in the patient's body and, with guidance from the engineered receptors, recognize and kill cancer cells that harbor the surface antigen.

SUMMARY

Aspects of the disclosure relate to methods for determining whether or not a subject is likely to respond to certain adoptive cell therapies (e.g., chimeric antigen receptor (CAR) T-cell therapy, etc.) and/or other immunotherapies. The disclosure is based, in part, on the recognition that cancer cells (e.g., solid tumor cells, hematological cancer cells, etc.) obtained from a subject may be used to identify a tumor microenvironment (TME) type of the subject (e.g., a blood cancer or lymphoma TME type, solid tumor cancer TME type, etc.), which is indicative of whether or not the subject is likely to respond to adoptive cell therapies, for example treatment with chimeric antigen receptor (CAR) T-cell therapy.

The inventors have recognized that gene expression data of a sample obtained from a cancer patient can be processed to produce certain molecular functional signatures (for example molecular functional expression signatures (MFES) and lymphoma microenvironment (LME) signatures) that reflect the biological processes occurring in the tumor microenvironment (TME) of the subject. In some embodiments, the signatures are produced by processing gene expression data for a plurality of gene groups, where each gene group comprises genes that are involved in the particular biological process encompassed by that gene group (e.g., genes involved in angiogenesis may be part of an Angiogenesis gene group). Processing gene expression data in this way, across gene groups that underlie several different biological processes, provides a snapshot of the tumor microenvironment (TME) of the subject. While previous methods of assessing biomarkers to identify appropriate therapies have been described, the inventors believe that the combinations of gene groups and gene group genes utilized in the invention are novel and unconventional because they allow characterization of the TME as a whole instead of as a collection of discreet biological processes.

Furthermore, the inventors have discovered that across certain cancers, for example blood cancers or solid cancers, or within certain cancers (e.g., lymphomas), these signatures can be categorized into four main types which are indicative of a subject's 1) prognosis (e.g., progression-free survival at 24-months; "PFS24"), and/or 2) likelihood of responding to a particular therapeutic intervention (e.g., adoptive cell transfer therapies, such as CAR-T therapy). Without wishing to be bound by any particular theory, the predictive power of the tumor microenvironment (TME) typing methods described herein relates to the connection between the signatures developed by the inventors and underlying tumor microenvironment biology of the subject.

The methods described herein offer several advantages and improvements to currently existing prognosis and therapeutic agent selection techniques. First, because the signatures and TME types described herein reflect the underlying TME biology of the subject, methods described herein provide physicians with increased confidence in prescribing CAR-T therapies to certain populations of patients that may not have a high response rate to first-line therapeutics (e.g., rituximab). Second, classification of patients by TME type may improve clinical trial design and efficiency by allowing selection of patients who are likely to respond to CAR-T therapy, and excluding subjects having TME types indicative of a lower response to CAR-T therapy.

Aspects of the disclosure relate to methods, systems, computer-readable storage media, and graphical user interfaces (GUIs) that can be used for determining whether or not a subject is likely to respond to an adoptive cell transfer therapy. In some aspects, the disclosure provides a method for determining whether or not a subject is likely to respond to an adoptive cell transfer therapy (e.g., chimeric antigen receptor (CAR) T-cell therapy), comprising: using at least one computer hardware processor to perform: obtaining sequencing data for a subject having, suspected of having, or at risk of having a solid tumor cancer or a blood cancer; determining a molecular-functional expression signature (MFES) for the subject using the sequencing data; identifying, from among tumor microenvironment (TME) types, a TME type associated with the cancer using the determined MF expression signature of the subject; and determining whether the subject is likely to respond to the adoptive cell transfer therapy based at least in part on the identified TME type.

In some embodiments, adoptive cell transfer therapy is a CAR T-cell therapy.

In some embodiments, a subject is a human.

In some embodiments, sequencing data is obtained from one or more biological samples obtained from the subject. In some embodiments, the biological sample comprises a blood sample or tissue sample. In some embodiments, a tissue sample comprises a tumor tissue sample.

In some embodiments, the sequencing data comprises RNA sequencing data. In some embodiments, the sequencing data comprises at least 5 kb of DNA. In some embodiments, the sequencing data comprises at least 5 kb of RNA.

In some embodiments, determining the molecular-functional (MF) expression signature comprises processing the sequencing data to obtain gene expression data.

In some embodiments, determining the molecular-functional (MF) expression signature comprises using the sequencing data to determine gene group expression scores for at least one (e.g., 1, 2, 3, 4, 5, or more) of the following gene groups: Lymphatic endothelium (LEC), Angiogenesis (VEC), Cancer-associated fibroblasts (CAF), Fibroblastic reticular cells (FRC), Matrix (ECM), Matrix Remodeling (ECM remodeling), Granulocyte traffic, Protumor cytokines (IS cytokines), Follicular Dendritic Cells (FDC), Macrophages, M1 signature (activated M1), Effector cell traffic (T cell traffic), Major histocompatibility complex II (MHC-II), Major histocompatibility complex I (MHC-I), Follicular B helper T cells (TFH), Regulatory T cells (Treg), T cells (TIL), Checkpoint inhibition (IS checkpoints), Natural Killer Cells (NK cells), B cell traffic, Benign B cells (B cells), Tumor proliferation rate (cell proliferation), Nuclear factor kappa B (NFkB), Phosphoinositide 3-kinase (PI3K), and p53.

In some embodiments, determining the molecular-functional (MF) expression signature comprises using the sequencing data to determine a gene group expression score for one or more genes (e.g., 1, 2, 3, 4, 5, or more) of the following gene groups using gene expression data from one or more genes (e.g., 1, 2, 3, 4, 5, or more) of the respective following sets of genes: Lymphatic endothelium (LEC): JAM3, PPPJR13B, CXL12, PDPN, CXADR, FLT4, CCL21, FOXC2, EDNRB, LYVE1, PROX1, SOX8, and JAM2; Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2; Cancer-associated fibroblasts (CAF): COL1A1, MMP2, LGALS1, MMP7, LRP1, CD248, S100A4, PAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2; Fibroblastic reticular cells (FRC): PDGFRA, ACTA2, ICAM1, NT5E, VIM, PDPN, THY1, DES, VCAM1, PTGS2, and LTBR; Matrix (ECM): COL1A1, COL3A1, LGALS7, FN1, VTN, COL1A2, and COL4A1; Matrix Remodeling (ECM remodeling): TIMP1, TIMP2, MMP2, MMP9, and CA9; Granulocyte traffic: KITLG, CXCL8, CXCR1, CXCR2, CXCL5, KIT, CCL11, CCR3, CXCL1, and CXCL2; Protumor cytokines (IS cytokines): CCL4, IL6, TNFSF13B, MIF, CXCL8, IL22, and IL10; Follicular Dendritic Cells (FDC): PDPN, TNFRSFIA, LTBR, FDCSP, (CLU, PRNP, and BST1; Macrophages: IL10, MSR1, ARG1, CSF1R, CD163, MRC1, and CSF1; M1 signature (activated M1): TNF, NOS2, IL1B, and CMKLR1; Effector cell traffic (T cell traffic): CXCL11, CXCL10, CXCL9, CXCR3, CX3CL1, CCL5, and CX3CR1; Major histocompatibility complex II (MHC-II): HLA-DQB1, HLA-DIPB1, HLA-DIPA1, HLA-IDRA, HLA-DQA1, HLA-DMA, HLA-DRB1, and HLA-DMB; Major histocompatibility complex I (MHC-I): TAP1, HLA-C, B2M, HLA-B, HLA-A, and TAP2; Follicular B helper T cells (TFH): CD40LG, SH2D1A, CD84, CXCR5, IL4, IL6, MAF, BCL6, IL21, and ICOS; Regulatory T cells (Treg): CCR8, CTIA4, IKZF2, IKZF4, FOXP3, IL10, and INFRSF18; T cells (TIL): CD3D, TRAT1, TBX21, TRBC2, ITK, CD28, CD3E, TRBC1, TRA4C, and CD3G; Checkpoint inhibition (IS checkpoints): CTIA4, HAVCR2, CD274, PDCD1, BTLA, TIGIT, PDCDILG2, and LAG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1; B cell traffic: CXCL13, CXCR5, CCR6, and CCL20; Benign B cells (B cells): CD79B, M-S4A1, STAP1, TNFRSF17, CD24, CD22, TNFRSF13B, BLK, CD19, PAX5, CD79A, TNFRSF13C, and FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1.

In some embodiments, the gene group expression score for one or more genes (e.g., 1, 2, 3, 4, 5, or more) is from the gene set of Major histocompatibility complex I (MHC-I).

In some embodiments, the gene group expression score for one or more genes (e.g., 1, 2, 3, 4, 5, or more) is from the gene set of Major histocompatibility complex II. (MHC-II).

In some embodiments, the gene group expression score for one or more genes (e.g., 1, 2, 3, 4, 5, or more) is from the gene set of Effector cell traffic (T cell traffic).

In some embodiments, the gene group expression score for one or more genes (e.g., 1, 2, 3, 4, 5, or more) is from the gene set of Regulatory T cells (Treg).

In some embodiments, the gene group expression score for one or more genes (e.g., 1, 2, 3, 4, 5, or more) is from the gene set of M1 signature (activated M1).

In some embodiments, the gene group expression score for one or more genes (e.g., 1, 2, 3, 4, 5, or more) is from the gene set of Checkpoint inhibition (IS checkpoints).

In some embodiments, the gene group expression score for one or more genes (e.g., 1, 2, 3, 4, 5, or more) is from the gene set of T cells (TIL).

In some embodiments, the gene group expression score for one or more genes (e.g., 1, 2, 3, 4, 5, or more) is from the gene set of Macrophages.

In some embodiments, the gene group expression score for one or more genes (e.g., 1, 2, 3, 4, 5, or more) is from the gene set of Cancer-associated fibroblasts (CAF).

In some embodiments, the gene group expression score for one or more genes (e.g., 1, 2, 3, 4, 5, or more) is from the gene set of Matrix (ECM).

In some embodiments, the gene group expression score for one or more genes (e.g., 1, 2, 3, 4, 5, or more) is from the gene set of Matrix Remodeling (ECM remodeling).

In some embodiments, the gene group expression score for one or more genes (e.g., 1, 2, 3, 4, 5, or more) is from the gene set of Angiogenesis (VEC).

In some embodiments, the gene group expression score for one or more genes (e.g., 1, 2, 3, 4, 5, or more) is from the gene set of Tumor proliferation rate (cell proliferation).

In some embodiments, the gene group expression score for one or more genes (e.g., 1, 2, 3, 4, 5, or more) is from the gene set of EMT signature.

In some embodiments, the gene group expression score for one or more genes (e.g., 1, 2, 3, 4, 5, or more) is from the gene set of Lymphatic endothelium (LEC).

In some embodiments, determining the molecular-functional (MF) expression signature comprises using the sequencing data to determine a gene group expression score for the Lymphatic endothelium (LEC) gene group using one or more (e.g., 1, 2, 3, 4, 5, or more) genes selected from: JAM3, PPP1R13B, CXCL12, PDPN, CXADR, FLT4, CCL21, FOXC2, EDNRB, LYVE1, PROX1, SOX18, and JAM2.

In some embodiments, determining the molecular-functional (MF) expression signature comprises using the sequencing data to determine a gene group expression score for the Angiogenesis (VEC) gene group using one or more (e.g., 1, 2, 3, 4, 5, or more) genes selected from: CDH5, PGF, PDGFC, TEK, VEGFC, CXCL8, VWF, CXCR2, ANGPT1, CXCL5, FLT1, VEGFA, KDR, VEFGFB, and ANGP2.

In some embodiments, determining the molecular-functional (MF) expression signature comprises using the sequencing data to determine a gene group expression score for the Cancer-associated fibroblasts (CAF) gene group using one or more (e.g., 1, 2, 3, 4, 5, or more) Cancer-associated fibroblasts genes selected from: COL1A1, MMP2, LGALS1, MMP7, LRP1, CD248, S100A4, FAP, FGF2, MMP9, CTGF, ACTA2, FN1, COL1A2, COL5A1, COL6A1, MMP3, CAA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2.

In some embodiments, determining the molecular-functional (MF) expression signature comprises using the sequencing data to determine a gene group expression score for the Fibroblastic reticular cells (FRC) gene group using one or more (e.g., 1, 2, 3, 4, 5, or more) genes selected from: PDGFRA, ACTA2, ICAM1, NT5E, VIM, PDPN, THY1, DES, VCAM1, PTGS2, and LTBR.

In some embodiments, determining the molecular-functional (MF) expression signature comprises using the sequencing data to determine a gene group expression score for the Matrix (ECM) gene group using one or more (e.g., 1, 2, 3, 4, 5, or more) genes selected from: COL1A1, COL3A1, LGALS7, FN1, VTN, COL1A2, and COL4A1.

In some embodiments, determining the molecular-functional (MF) expression signature comprises using the sequencing data to determine a gene group expression score for the Matrix Remodeling (ECM remodeling) gene group using one or more (e.g., 1, 2, 3, 4, 5, or more) genes selected from: TIMP1, TIMP2, MMP2, MMP9, and CA9.

In some embodiments, determining the molecular-functional (MF) expression signature comprises using the sequencing data to determine a gene group expression score for the Granulocyte traffic gene group using one or more (e.g., 1, 2, 3, 4, 5, or more) genes selected from: KITLG, CXCL8, CXCR1, CXCR2, CXCL5, KIT, CCL11, CCR3, CXCL1, and CXCL2.

In some embodiments, determining the molecular-functional (MF) expression signature comprises using the sequencing data to determine a gene group expression score for the Protumor cytokines (IS cytokines) gene group using one or more (e.g., 1, 2, 3, 4, 5, or more) genes selected from: CCL4, IL6, TNFSF13B, MIF, CXCL8, IL22, and IL10.

In some embodiments, determining the molecular-functional (MF) expression signature comprises using the sequencing data to determine a gene group expression score for the Follicular Dendritic Cells (FDC) gene group using one or more (e.g., 1, 2, 3, 4, 5, or more) genes selected from: PDPN, TNFRSFIA, LTBR, FDCSP, CLU, PRNP, and BST.

In some embodiments, determining the molecular-functional (MF) expression signature comprises using the sequencing data to determine a gene group expression score for the Macrophages gene group using one or more (e.g., 1, 2, 3, 4, 5, or more) genes selected from: IL10, MSR1, ARG1, CSF1R, CD163, MRC1, and CSF1.

In some embodiments, determining the molecular-functional (MF) expression signature comprises using the sequencing data to determine a gene group expression score for the M1 signature (activated M1) gene group using one or more (e.g., 1, 2, 3, 4, or more) genes selected from: TNF, NOS2, IL1B, and CMKLR1.

In some embodiments, determining the molecular-functional (MF) expression signature comprises using the sequencing data to determine a gene group expression score for the Effector cell traffic (T cell traffic) gene group using one or more (e.g., 1, 2, 3, 4, 5, or more) genes selected from: CXCL11, CXCL10, CXCL9, CXCR3, CX3CL1, CCL5, and CX3CR1.

In some embodiments, determining the molecular-functional (MF) expression signature comprises using the sequencing data to determine a gene group expression score for the Major histocompatibility complex II (MHC-II) gene group using one or more (e.g., 1, 2, 3, 4, 5, or more) genes selected from: HLA-DQB1, HLA-DPB1, HLA-DPA1, HLA-DRA, HLA-DQA1, HLA-DMA, HLA-DRB1, and HLA-DMB.

In some embodiments, determining the molecular-functional (MF) expression signature comprises using the sequencing data to determine a gene group expression score for the Major histocompatibility complex I (MHC-I) gene group using one or more (e.g., 1, 2, 3, 4, 5, or more) genes selected from: TAP1, HLA-C, B2M, HLA-B, HLA-A, and TAP2.

In some embodiments, determining the molecular-functional (MF) expression signature comprises using the sequencing data to determine a gene group expression score for the Follicular B helper T cells (TFH) gene group using one or more (e.g., 1, 2, 3, 4, 5, or more) genes selected from: CD40LG, SH2D1A, CD84, CXCR5, IL4, IL6, MAF, BCL6, IL21, and ICOS.

In some embodiments, determining the molecular-functional (MF) expression signature comprises using the sequencing data to determine a gene group expression score for the Regulatory T cells (Treg) gene group using one or more (e.g., 1, 2, 3, 4, 5, or more) genes selected from: CCR8, CTLA4, IKZF2, IKZF4, FOXP3, IL10, and TNFRSF18.

In some embodiments, determining the molecular-functional (MF) expression signature comprises using the sequencing data to determine a gene group expression score for the T cells (TIL) gene group using one or more (e.g., 1, 2, 3, 4, 5, or more) genes selected from: CD3D, TRAT1, TBX21, TRBC2, ITK, CD28, CD3E, TRBC1, TRAC, and CD3G.

In some embodiments, determining the molecular-functional (MF) expression signature comprises using the sequencing data to determine a gene group expression score for the Checkpoint inhibition (IS checkpoints) gene group using one or more (e.g., 1, 2, 3, 4, 5, or more) genes selected from: CTLA4, HAVCR2, CD274, PDCD1, BTLA, TIGIT, PDCD1LG2, and LAG3.

In some embodiments, determining the molecular-functional (MF) expression signature comprises using the sequencing data to determine a gene group expression score for the Natural Killer Cells (NK cells) gene group using one or more (e.g., 1, 2, 3, 4, 5, or more) genes selected from: SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1.

In some embodiments, determining the molecular-functional (MF) expression signature comprises using the sequencing data to determine a gene group expression score for the B cell traffic gene group using one or more (e.g., 1, 2, 3, 4, 5, or more) genes selected from: CXCL13, CXCR5, CCR6, and CCL20.

In some embodiments, determining the molecular-functional (MF) expression signature comprises using the sequencing data to determine a gene group expression score for the Benign B cells (B cells) gene group using one or more (e.g., 1, 2, 3, 4, 5, or more) genes selected from: CD79B, MS4A1, STAP1, TNFRSF17, CD24, CD22, INFRSF13B, BLK, CD19, PAX5, CD79A, TNFRSF13C, and FCRL5.

In some embodiments, determining the molecular-functional (MF) expression signature comprises using the sequencing data to determine a gene group expression score for the Tumor proliferation rate (cell proliferation) gene group using one or more (e.g., 1, 2, 3, 4, 5, or more) genes selected from: MCM6, AURKB, ESCO2, CCNB1, AURKA, MKI67, CCND1, CCNE1, MCM2, MYBL2, E2F1, CETN3, CDK2, PLK1, and BUB1.

In some embodiments, determining the molecular-functional (MF) expression signature comprises using the sequencing data to determine gene group expression scores for each of the genes of each of the following gene groups using gene expression data from each gene of the respective following sets of genes: Lymphatic endothelium (LEC): JAM3, PPP1R13B, CXCL12, PDPN, CXADR, FLT4, CCL21, FOXC2, EDNRB, LYVE1, PROX1, SOX18, and JAM2; Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2; Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2; Fibroblastic reticular cells (FRC): PDGFRA, ACTA2, ICAM1, NT5E, VIM, PDPN, THY1, DES, VCAM1, PTGS2, and LTBR; Matrix (ECM): COL1A1, COL3A1, LGALS7, FN1, VTN, COL1A2, and COL4AJ; Matrix Remodeling (ECM remodeling): TIMP1, TIMP2, MMP2, MMP9, and CA9; Granulocyte traffic: KITLG, CXCL8, CXCR1, CXCR2, CXCL5, KIT, CCL11, CCR3, CXCL1, and CXCL2; Protumor cytokines (IS cytokines): CCL4, IL6, TNFSF13B, MIF, CXCL8, IL22, and IL10; Follicular Dendritic Cells (FDC): PDPN, TNFRSFIA, LTBR, FDCSP, CLU, PRNP, and BST1; Macrophages: IL10, MSR1, ARG1, CSF1R, CD163, MRC1, and CSF1; M1 signature (activated M1): TNF, NOS2, IL1B, and CMKLR1; Effector cell traffic (T cell traffic): CXCL11, CXCL10, CXCL9, CXCR3, CX3CL1, CCL5, and CX3CR1; Major histocompatibility complex II (MHC-II): HLA-DQB1, HLA-DPB1, HLA-DPA1, HLA-DRA, HLA-DQA1, HLA-DMA, HLA-DRB1, and HLA-DMB; Major histocompatibility complex I (MHC-I): TAP1, HLA-C, B2M, HLA-B, HLA-A, and TAP2; Follicular B helper T cells (TFH): CD40LG, SH2D1A, CD84, CXCR5, IL4, IL6, MAF, BCL6, IL21, and ICOS; Regulatory T cells (Treg): CCR8, CTLA4, IKZF2, IKZF4, FOXP3, IL10, and TNFRSF18; T cells (TIL): CD3D, TRAT1, TBX21, TRBC2, ITK, CD28, CD3E, TRBC1, TRAC, and CD3G; Checkpoint inhibition (IS checkpoints): CTLA4, HAVCR2, CD274, PDCD1, BTLA, TIGIT, PDCD1LG2, and LG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1; B cell traffic: CXCL13, CXCR5, CCR6, and CCL20; Benign B cells (B cells): CD79B, MS4A1, STAP1, TNFRSF17, CD24, CD22, TNFRSF13B, BLK, CD19, PAX5, CD79A, TNFRSF13C, and FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1. In some embodiments, determining gene group expression scores for each of the genes comprises determining the gene expression data that is available. For example, the available gene expression data may include all genes in the gene sets as disclosed herein. In some embodiments, the available gene expression data may not include all genes in the gene sets as disclosed herein.

In some embodiments, a tumor microenvironment (TME) type associated with the cancer (e.g., a blood cancer or lymphoma, or a solid tumor cancer) is selected from type A, type B, type C, and type D.

In some embodiments, identifying the TME type comprises associating the MFES of the subject with a MFES cluster previously determined that is selected from a type A MFES cluster, a type B MFES cluster, a type C MFES cluster, and a type D MFES cluster.

In some embodiments, the adoptive cell transfer therapy is a CAR T-cell therapy, the subject has a blood cancer and the determining whether the subject is likely to respond to CAR T-cell therapy comprises: determining that the subject is not likely to respond to CAR T-cell monotherapy if the identified tumor type is blood cancer or lymphoma type A; determining that the subject is likely to respond to CAR T-cell monotherapy if the identified tumor type is blood cancer or lymphoma type B; determining that the subject is not likely to respond to CAR T-cell monotherapy if the identified tumor type is blood cancer or lymphoma type C; or determining that the subject is not likely to respond to CAR T-cell monotherapy if the identified tumor type is blood cancer or lymphoma type D.

In some embodiments, the adoptive cell transfer therapy is a CAR T-cell therapy, a subject has a solid tumor cancer and the determining whether the subject is likely to respond to CAR T-cell therapy comprises: determining that the subject is not likely to respond to CAR T-cell monotherapy if the identified tumor type is solid tumor cancer type A; determining that the subject is likely to respond to CAR T-cell monotherapy if the identified tumor type is solid tumor cancer type B; determining that the subject is not likely to respond to CAR T-cell monotherapy if the identified tumor type is solid tumor cancer type C; or determining that the subject is not likely to respond to CAR T-cell monotherapy if the identified tumor type is solid tumor cancer type D.

In some embodiments, a CAR T-cell expresses an antigen binding domain that targets CD19, CD20, or CD30.

In some embodiments, a subject has a blood cancer.

In some embodiments, a subject has a lymphoma. In some embodiments, the lymphoma is diffuse large B cell lymphoma (DLBCL).

In some embodiments, a subject has leukemia. In some embodiments, a subject has a solid cancer. In some embodiments, the subject has melanoma.

In some embodiments, the method further comprises administering a CAR-T therapy to the subject when it is determined that the subject is likely to respond to the CAR-T therapy.

In some embodiments, the method further comprises administering to the subject one or more therapeutic agents that are not and adoptive cell transfer therapy. In some embodiments, the one or more therapeutic agents comprise a small molecule, peptide, protein, antibody, inhibitory nucleic acid, mRNA, or any combination thereof. In some embodiments, the one or more therapeutic agents comprises a CD137 activator, PI3K delta/gamma inhibitor, immune checkpoint inhibitor, EZH2 inhibitor, BCL2 inhibitor, immunomodulator, anti-angiogenic agent, TGFBR2 inhibitor, WNT inhibitor, cytokine therapy, BKT inhibitors, personalized cancer vaccine, or any combination thereof. In some embodiments, the one or more therapeutic agents comprises Utomilumab, Lenalidomide, Rituximab, Rituximab+Lenalidomide, Umbralisib, nivolumab, ipilimumab, Tazemetostat, venetoclax, a TLR 1, 2, 7, or 9 agonist, Azacitidine, Ibrutinib, Selinexor, Utomilumab, IL2, IFNa, or any combination thereof.

In some embodiments, a method for determining whether or not a subject is likely to respond to an adoptive cell transfer therapy further comprising producing a report. In some embodiments, producing a report comprises (i) a recommendation to administer an adoptive cell transfer therapy to a subject that is likely to respond to the adoptive cell transfer therapy; or (ii) a recommendation to administer a non-adoptive cell transfer therapy to a subject that is unlikely to respond to an adoptive cell transfer therapy.

In some aspects, the disclosure provides a method of treating diffuse large B cell lymphoma (DLBCL) in a subject in need thereof by administering to the subject an adoptive cell therapy based upon a determination that the subject has a type A tumor microenvironment (TME) or type D TME.

In some aspects, the present disclosure provides an adoptive cell therapy for use in treating diffuse large B cell lymphoma (DLBCL) in a subject in need thereof, wherein the subject has been determined using a method described herein as likely to respond to the adoptive cell therapy.

In some aspects, the present disclosure provides an adoptive cell therapy for use in treating diffuse large B cell lymphoma (DLBCL) in a subject in need thereof, wherein the subject has been determined using a method described herein as having a type A TME or a type D TME.

In some embodiments, a subject has not previously been treated for DLBCL. In some embodiments, a subject has not previously been administered a CD20-targeting agent. In some embodiments, the subject has not previously been administered rituximab.

In some embodiments, a subject does not have a DLBCL type selected from DHIT+/MYC+, EZB, and A53.

In some embodiments, an adoptive cell therapy comprises a CAR T-cell therapy.

In some embodiments, the determination that the subject has a type D TME has been made according to a method comprising: using at least one computer hardware processor to perform: obtaining sequencing data from a biological sample obtained from the subject; determining a molecular-functional (MF) expression signature for the subject using the sequencing data; and identifying that the subject has a type D TME using the determined MF expression signature for the subject.

In some aspects, the disclosure provides a method of treating a solid tumor cancer in a subject in need thereof, the method comprising administering to the subject an adoptive cell therapy based upon a determination that the subject has a type A tumor microenvironment (TME), type B TME, or type D TME.

In some aspects, an adoptive cell therapy for use in treating a solid tumor cancer in a subject in need thereof, wherein the subject has been determined using a method described herein as likely to respond to the adoptive cell therapy.

In some aspects, an adoptive cell therapy for use in treating a solid tumor cancer in a subject in need thereof, wherein the subject has been determined using a method described herein as having a type A TME, a type B TME, or a type D TME.

In some embodiments, an adoptive cell therapy comprises a CAR T-cell therapy.

In some embodiments, the determination of the subject's TME type has been made according to a method comprising: using at least one computer hardware processor to perform: obtaining sequencing data from a biological sample obtained from the subject; determining a molecular-functional (MF) expression signature for the subject using the sequencing data; and identifying that the subject has a type A, TME, type B TME, or type D TME using the determined MF expression signature for the subject.

In some embodiments, determining the molecular-functional (MF) signature comprises processing the sequencing data to obtain gene expression data.

In some aspects, the disclosure provides a method of treating a solid tumor cancer in a subject in need thereof, the method comprising administering to the subject a therapeutic agent other than a CAR T-cell therapy based on a determination that the subject has a solid tumor cancer type C tumor microenvironment (TME).

In some aspects, a therapeutic agent for use in treating a solid tumor cancer in a subject, wherein the subject has been determined using a method described herein as unlikely to respond to the CAR T-cell therapy.

In some aspects, a therapeutic agent for use in treating a solid tumor cancer in a subject, wherein the subject has been determined using a method described herein as having a type C TME.

In some embodiments, the determination that the subject has a type C TME has been made according to a method comprising: using at least one computer hardware processor to perform: obtaining sequencing data from a biological sample obtained from the subject; determining a molecular-functional (MF) expression signature for the subject using the sequencing data; and identifying that the subject has a type C TME using the determined MF expression signature for the subject.

In some aspects, the disclosure provides a method of treating a blood cancer or lymphoma in a subject in need thereof, the method comprising administering to the subject a therapeutic agent other than a CAR T-cell therapy based on a determination that the subject has a blood cancer type A tumor microenvironment (TME).

Aspects of the disclosure relate to methods, systems, computer-readable storage media, and graphical user interfaces (GUIs) that are useful for characterizing subjects having certain cancers, for example lymphomas. The disclosure is based, in part, on methods for determining the lymphoma microenvironment (LME) type of a lymphoma (e.g., Diffuse Large B Cell Lymphoma (DLBCL)) subject. In some embodiments, methods comprise identifying the subject's prognosis, such as overall survival (OS) and/or progression-free survival (PFS), based upon the LME type determination. In some embodiments, methods described herein are useful for stratifying patient risk or predicting patient survival.

Accordingly, in some aspects, the disclosure provides a method for determining a Diffuse Large B cell lymphoma (DLBCL) microenvironment (LME) type of a subject, the method comprising using at least one computer hardware processor to perform:

obtaining sequencing data for a subject having, suspected of having, or at risk of having a DLBCL; determining a LME signature for the subject using the sequencing data, wherein the LME signature is obtained using: (i) a gene expression signature comprising a plurality of gene group expression scores for a respective plurality of gene groups; and/or (ii) one or more PROGENY pathway scores for the sequencing data; and assigning, from a plurality of LME types, an LME type to the subject using the LME signature.

In some aspects, the disclosure provides a method for providing a prognosis, predicting survival or stratifying patient risk of a subject suspected of having, or at risk of having a Diffuse Large B cell lymphoma (DLBCL), the method comprising determining a DLBCL microenvironment (LME) type of the subject as described herein.

In some embodiments, the plurality of gene groups includes at least three gene groups listed in Table 3, and wherein obtaining the LME signature for the subject comprises determining at least three gene groups listed in Table 3 using one or more genes listed in Table 3 for each of the respective groups.

In some embodiments, obtaining the LME signature for the subject comprises using the sequencing data to determine gene group expression scores for one or more gene groups listed in Table 3, each of which includes determining one or more gene groups listed in Table 3 using one or more genes listed in Table 3 for each of the respective groups.

In some embodiments, the one or more PROGENY pathway scores comprises NFkB, PI3K, and/or p53 signaling signatures.

In some embodiments, the plurality of LME types includes LME-A type, LME-B type, LME-C type, and LME-D type.

In some embodiments, the plurality of gene groups includes at least three of the following gene groups, and wherein obtaining the LME signature for the subject comprises: In some embodiments, determining the molecular-functional (MF) expression signature comprises using the sequencing data to determine gene group expression scores for at least one (e.g., 1, 2, 3, 4, 5, or more) of the following gene groups: Lymphatic endothelium (LEC), Angiogenesis (VEC), Cancer-associated fibroblasts (CAF), Fibroblastic reticular cells (FRC), Matrix (ECM), Matrix Remodeling (ECM remodeling), Granulocyte traffic, Protumor cytokines (IS cytokines), Follicular Dendritic Cells (FDC), Macrophages, M1 signature (activated M1), Effector cell traffic (T cell traffic), Major histocompatibility complex II (MHC-II), Major histocompatibility complex I (MHC-I), Follicular B helper T cells (TFH), Regulatory T cells (Treg), T cells (TL), Checkpoint inhibition (IS checkpoints), Natural Killer Cells (NK cells), B cell traffic, Benign B cells (B cells), Tumor proliferation rate (cell proliferation), Nuclear factor kappa B (NFkB), Phosphoinositide 3-kinase (PI3K), and p53.

In some embodiments, determining the lymphoma microenvironment (LME) signature comprises using the sequencing data to determine gene group expression scores for one or more genes (e.g., 1, 2, 3, 4, 5, or more) of the following gene groups using gene expression data from one or more genes (e.g., 1, 2, 3, 4, 5, or more) of the respective following sets of genes: Lymphatic endothelium (LEC): JAM3, PPP1R13B, CXCL12, PDPN, CXADR, FLT4, CCL21, FOXC2, EDNRB, LYVE1, PROX1, SOX18, and JAM2; Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2; Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2; Fibroblastic reticular cells (FRC): PDGFRA, ACTA2, ICAM1, NT5E, VIM, PDPN, THY1, DES, VCAM1, PTGS2, and LTBR; Matrix (ECM): COL1A1, COL3A/, LGALS7, FN1, VTN, COL1A2, and COL4A1; Matrix Remodeling (ECM remodeling): TIMP1, TIMP2, MMP2, MMP9, and CA9; Granulocyte traffic: KITLG, CCL8, CXCR1, CXCR2, CXCL5, KIT, CCL11, CCR3, CXCL1, and CXCL2; Protumor cytokines (IS cytokines): CCL4, IL6, TNFSF13B, MIF, CXCL8, IL22, and IL10; Follicular Dendritic Cells (FDC): PDPN, TNFRSF1A, LTBR, FDCSP, CLU, PRNP, and BST1; Macrophages: IL10, MSR1, ARG1, CSF1R, CD163, MRC1, and CSF1; M1 signature (activated M1): 7NF, NOS2, IL1B, and CMKLR1; Effector cell traffic (T cell traffic): CXCL11, CXCL10, CXCL9, CXCR3, CX3CL, CCL5, and CX3CR1; Major histocompatibility complex II (MHC-II): HLA-DQB1, HLA-DPB1, HLA-DPA1, HLA-DRA, HLA-DQA1, HLA-DMA, HLA-DRB1, and HLA-DMB; Major histocompatibility complex I (MHC-I): TAP1, HLA-C, B2M, HLA-B, HLA-A, and TAP2; Follicular B helper T cells (TFH): CD40LG, SH2D1A, CD84, CXCR5, IL4, IL6, MAF, BCL6, IL21, and ICOS; Regulatory T cells (Treg): (CCR8, CTIA4, IKZF2, IKZF4, FOXP3, IL10, and TNFRSF18; T cells (TIL): CD3D, TRAT1, TBX21, TRBC2, ITK, CD28, CD3E, TRBC1, TRAC, and CD3G; Checkpoint inhibition (IS checkpoints): CTLA4, HAVCR2, CD274, PDCD1, BTLA, TIGIT, PDCDILG2, and LAG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1; B cell traffic: CXCL13, CXCR5, CCR6, and CCL20; Benign B cells (B cells): CD79B, MS4A1, STAP1, TNFRSF17, CD24, CD22, TNFRSF13B, BLK, CD19, PAX5, CD79A, TNFRSF13C, and FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1.

In some embodiments, the gene group expression score for one or more genes (e.g., 1, 2, 3, 4, 5, or more) is from the gene set of Lymphatic endothelium (LEC).

In some embodiments, the gene group expression score for one or more genes (e.g., 1, 2, 3, 4, 5, or more) is from the gene set of Angiogenesis (VEC).

In some embodiments, the gene group expression score for one or more genes (e.g., 1, 2, 3, 4, 5, or more) is from the gene set of Cancer-associated fibroblasts (CAF).

In some embodiments, the gene group expression score for one or more genes (e.g., 1, 2, 3, 4, 5, or more) is from the gene set of Fibroblastic reticular cells (FRC).

In some embodiments, the gene group expression score for one or more genes (e.g., 1, 2, 3, 4, 5, or more) is from the gene set of Matrix (ECM).

In some embodiments, the gene group expression score for one or more genes (e.g., 1, 2, 3, 4, 5, or more) is from the gene set of Matrix Remodeling (ECM remodeling).

In some embodiments, the gene group expression score for one or more genes (e.g., 1, 2, 3, 4, 5, or more) is from the gene set of Follicular Dendritic Cells (FDC).

In some embodiments, the gene group expression score for one or more genes (e.g., 1, 2, 3, 4, 5, or more) is from the gene set of Macrophages.

In some embodiments, the gene group expression score for one or more genes (e.g., 1, 2, 3, 4, 5, or more) is from the gene set of M1 signature (activated M1).

In some embodiments, the gene group expression score for one or more genes (e.g., 1, 2, 3, 4, 5, or more) is from the gene set of Major histocompatibility complex I (MHC-I).

In some embodiments, the gene group expression score for one or more genes (e.g., 1, 2, 3, 4, 5, or more) is from the gene set of Major histocompatibility complex II. (MHC-II).

In some embodiments, the gene group expression score for one or more genes (e.g., 1, 2, 3, 4, 5, or more) is from the gene set of Follicular B helper T cells (TFH).

In some embodiments, the gene group expression score for one or more genes (e.g., 1, 2, 3, 4, 5, or more) is from the gene set of Regulatory T cells (Treg).

In some embodiments, the gene group expression score for one or more genes (e.g., 1, 2, 3, 4, 5, or more) is from the gene set of T cells (TIL).

In some embodiments, the gene group expression score for one or more genes (e.g., 1, 2, 3, 4, 5, or more) is from the gene set of Benign B cells (B cells).

In some embodiments, the gene group expression score for one or more genes (e.g., 1, 2, 3, 4, 5, or more) is from the gene set of Tumor proliferation rate (cell proliferation).

In some embodiments, determining the LME signature further comprises determining the PROGENY pathway scores for one or more of Nuclear factor kappa B (NFkB), Phosphoinositide 3-kinase (PI3K), and p53. In some embodiments, determining the molecular-functional (MF) expression signature further comprises determining the PROGENY pathway scores for each of Nuclear factor kappa B (NFkB), Phosphoinositide 3-kinase (PI3K), and p53.

In some embodiments, determining the LME signature comprises using the sequencing data to determine a gene group expression score for the Lymphatic endothelium (LEC) gene group using one or more (e.g., 1, 2, 3, 4, 5, or more) genes selected from: JAM3, PPP1R13B, CXCL12, PDPN, CXADR, FLT4, CCL21, FOXC2, EDNRB, LYVE1, PROX1, SOX18, and JAM2.

In some embodiments, determining the LME signature comprises using the sequencing data to determine a gene group expression score for the Angiogenesis (VEC) gene group using one or more (e.g., 1, 2, 3, 4, 5, or more) genes selected from: CDH5, PGF, PDGFC, TEK, VEGFC, CXCL8, VWF, CXCR2, ANGPT1, CXCL5, FLT1, VEGFA, KDR, VEGFB, and ANGPT2.

In some embodiments, determining the LME signature comprises using the sequencing data to determine a gene group expression score for the Cancer-associated fibroblasts (CAF) gene group using one or more (e.g., 1, 2, 3, 4, 5, or more) Cancer-associated fibroblasts genes selected from: COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2.

In some embodiments, determining the LME signature comprises using the sequencing data to determine a gene group expression score for the Fibroblastic reticular cells (FRC) gene group using one or more (e.g., 1, 2, 3, 4, 5, or more) genes selected from: PDGFRA, ACTA2, ICAM1, NT5E, VIM, PDPN, THY1, DES, VCAM1, PTGS2, and LTBR.

In some embodiments, determining the LME signature comprises using the sequencing data to determine a gene group expression score for the Matrix (ECM) gene group using one or more (e.g., 1, 2, 3, 4, 5, or more) genes selected from: COL1A1, COL3A1, LGALS7, FN1, VTN, COL1A2, and COL4AL.

In some embodiments, determining the LME signature comprises using the sequencing data to determine a gene group expression score for the Matrix Remodeling (ECM remodeling) gene group using one or more (e.g., 1, 2, 3, 4, 5, or more) genes selected from: TIMP1, TIMP2, MMP2, MMP9, and CA9.

In some embodiments, determining the LME signature comprises using the sequencing data to determine a gene group expression score for the Granulocyte traffic gene group using one or more (e.g., 1, 2, 3, 4, 5, or more) genes selected from: KITLG, CXCL8, CXCR1, CXCR2, CXCL5, KIT, CCL11, CCR3, CXCL1, and CXCL2.

In some embodiments, determining the LME signature comprises using the sequencing data to determine a gene group expression score for the Protumor cytokines (IS cytokines) gene group using one or more (e.g., 1, 2, 3, 4, 5, or more) genes selected from: CCL4, IL6, TNFSF13B, MIF, CXCL8, IL22, and IL10.

In some embodiments, determining the LME signature comprises using the sequencing data to determine a gene group expression score for the Follicular Dendritic Cells (FDC) gene group using one or more (e.g., 1, 2, 3, 4, 5, or more) genes selected from: PDPN, TNFRSFIA, LTBR, FDCSP, CLU, PRNP, and BST1.

In some embodiments, determining the LME signature comprises using the sequencing data to determine a gene group expression score for the Macrophages gene group using one or more (e.g., 1, 2, 3, 4, 5, or more) genes selected from: IL10, MSR1, ARG1, CSF1R, CD163, MRC1, and CSF1.

In some embodiments, determining the LME signature comprises using the sequencing data to determine a gene group expression score for the M1 signature (activated M1) gene group using one or more (e.g., 1, 2, 3, 4, or more) genes selected from: TNF, NOS2, IL1B, and CMKLR1.

In some embodiments, determining the LME signature comprises using the sequencing data to determine a gene group expression score for the Effector cell traffic (T cell traffic) gene group using one or more (e.g., 1, 2, 3, 4, 5, or more) genes selected from: CXCL11, CXCL10, CXCL9, CXCR3, CX3CL1, CCL5, and CX3CR1.

In some embodiments, determining the LME signature comprises using the sequencing data to determine a gene group expression score for the Major histocompatibility complex II (MHC-II) gene group using one or more (e.g., 1, 2, 3, 4, 5, or more) genes selected from: HLA-DQB1, HLA-DPB1, HLA-DPA1, HLA-DRA, HLA-DQA1, HLA-DMA, HLA-DRB1, and HLA-DMB.

In some embodiments, determining the LME signature comprises using the sequencing data to determine a gene group expression score for the Major histocompatibility complex I (MHC-I) gene group using one or more (e.g., 1, 2, 3, 4, 5, or more) genes selected from: TAP1, HLA-C, B2M, HLA-B, HLA-A, and TAP2.

In some embodiments, determining the LME signature comprises using the sequencing data to determine a gene group expression score for the Follicular B helper T cells (TFH) gene group using one or more (e.g., 1, 2, 3, 4, 5, or more) genes selected from: CD40LG, SH2D1A, CD84, CXCR5, IL4, IL6, MAF, BCL6, IL21, and ICOS.

In some embodiments, determining the LME signature comprises using the sequencing data to determine a gene group expression score for the Regulatory T cells (Treg) gene group using one or more (e.g., 1, 2, 3, 4, 5, or more) genes selected from: CCR8, CTLA4, IKZF2, IKZF4, FOXP3, IL10, and TNFRSF18.

In some embodiments, determining the LME signature comprises using the sequencing data to determine a gene group expression score for the T cells (TIL) gene group using one or more (e.g., 1, 2, 3, 4, 5, or more) genes selected from: CD3D, TRAT1, TBX21, TRBC2, ITK, CD28, CD3E, TRBC1, TRAC, and CD3G.

In some embodiments, determining the LME signature comprises using the sequencing data to determine a gene group expression score for the Checkpoint inhibition (IS checkpoints) gene group using one or more (e.g., 1, 2, 3, 4, 5, or more) genes selected from: CTLA4, HAVCR2, CD274, PDCD1, BTLA, TIGIT, PDCDILG2, and LAG3.

In some embodiments, determining the LME signature comprises using the sequencing data to determine a gene group expression score for the Natural Killer Cells (NK cells) gene group using one or more (e.g., 1, 2, 3, 4, 5, or more) genes selected from: SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1.

In some embodiments, determining the LME signature comprises using the sequencing data to determine a gene group expression score for the B cell traffic gene group using one or more (e.g., 1, 2, 3, 4, 5, or more) genes selected from: CXCL13, CXCR5, CCR6, and CCL20.

In some embodiments, determining the LME signature comprises using the sequencing data to determine a gene group expression score for the Benign B cells (B cells) gene group using one or more (e.g., 1, 2, 3, 4, 5, or more) genes selected from: CD79B, MS4A1, STAP1, TNFRSF17, CD24, CD22, TNFRSF13B, BLK, CD19, PAX5, CD79A, TNFRSF13C, and FCRL5.

In some embodiments, determining the LME signature comprises using the sequencing data to determine a gene group expression score for the Tumor proliferation rate (cell proliferation) gene group using one or more (e.g., 1, 2, 3, 4, 5, or more) genes selected from: MCM6, AURKB, ESCO2, CCNB1, AURKA, MKI67, (CCND1, CCNE1, MCM2, MYBL2, E2F1, CETN3, CDK2, PLK1, and BUB1.

In some embodiments, determining the LME signature comprises using the sequencing data to determine gene group expression scores for each of the genes of each of the following gene groups using gene expression data from each gene of the respective following sets of genes: Lymphatic endothelium (LEC): JAM3, PPP1R13B, CXCL12, PDPN, CXADR, FLT4, CCL21, FOXC2, EDNRB, LYVE1, PROX1, SOX18, and JAM2; Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2; Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2; Fibroblastic reticular cells (FRC): PDGFRA, ACTA2, ICAM1, NT5E, VIM, PDPN, THY1, DES, VCAM1, PTGS2, and LTBR; Matrix (ECM): COL1A1, COL3A1, LGALS7, FN1, VTN, COL1A2, and COL4A1; Matrix Remodeling (ECM remodeling): TIMP1, TIMP2, MMP2, MMP9, and CA9; Granulocyte traffic: KITLG, CXCL8, CXCR1, CXCR2, CXCL5, KIT, CCL11, CCR3, CXCL1, and CXCL2; Protumor cytokines (IS cytokines): CCL4, IL6, TNFSF13B. MIF, CXCL8, IL22, and IL10; Follicular Dendritic Cells (FDC): PDPN, TNFRSF1A, LTBR, FDCSP, CLU, PRNP, and BST1; Macrophages: IL10, MSR1, ARG1, CSF1R, CD163, MRC1, and CSF1; M1 signature (activated M1): 7NF, NOS2, IL1B, and CMKLR1; Effector cell traffic (T cell traffic): CXCL11, CXCL10, (CXCL9, CXCR3, CX3CL1, CCL5, and CX3CR1; Major histocompatibility complex 11 (MHC-II): HLA-DQB1, HLA-DPB1, HLA-DPA1, HLA-DRA, HLA-DQA1, HLA-DMA, HLA-DRB1, and HLA-DMB; Major histocompatibility complex I (MHC-I): TAP1, HLA-C, B2M, HLA-B, HLA-A, and TAP2; Follicular B helper T cells (TFH): CD40LG, SH2D1A, CD84, CXCR5, IL4, IL6, MAF, BCL6, IL21, and ICOS;

Regulatory T cells (Treg): CCR8, CTLA4, IKZF2, IKZF4, FOXP3, IL10, and TNFRSF18; T cells (TIL): CD3D, TRAT1, TBX21, TRBC2, ITK, CD28, CD3E, TRBC1, TRAC, and CD3G; Checkpoint inhibition (IS checkpoints): CTLA4, HAVCR2, CD274, PDCD1, BTLA, TIGIT, PDCD1LG2, and LAG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1; B cell traffic: CXCL13, CXCR5, CCR6, and CCL20; Benign B cells (B cells): CD793, MS4A1, STAP1, TNFRSF17, CD24, CD22, TNFRSF13B, BLK, CD19, PAX5, CD79A, TNFRSF13C, and FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1. In some embodiments, determining gene group expression scores for each of the genes comprises determining the gene expression data that is available. For example, the available gene expression data may include all genes in the gene sets as disclosed herein. In some embodiments, the available gene expression data may not include all genes in the gene sets as disclosed herein.

In some embodiments, the method further comprises administering to the subject one or more therapeutic agents that are not an adoptive cell transfer therapy. In some embodiments, the subject has a type C TME. In some embodiments, the one or more therapeutic agents comprise a small molecule, peptide, protein, antibody, inhibitory nucleic acid, mRNA, or any combination thereof. In some embodiments, the one or more therapeutic agents comprises a CD137 activator, PI3K delta/gamma inhibitor, immune checkpoint inhibitor, EZH2 inhibitor, BCL2 inhibitor, immunomodulator, anti-angiogenic agent, TGFBR2 inhibitor, WNT inhibitor, BKT inhibitors, cytokine therapy, personalized cancer vaccine, or any combination thereof. In some embodiments, the one or more therapeutic agents comprises Utomilumab, Lenalidomide, Rituximab, Rituximab+Lenalidomide, Umbralisib, nivolumab, ipilimumab, Tazemetostat, venetoclax, a TLR 1, 2, 7, or 9 agonist, Azacitidine, Ibrutinib, Selinexor, Utomilumab, IL2, IFNa, or any combination thereof.

In some aspects, the disclosure provides a method for treating a subject having Diffuse Large B cell lymphoma (DLBCL), the method comprising administering to a subject having been identified as having DLBCL characterized by a type LME-C or type LME-A one or more immunotherapeutic agents.

In some embodiments, the DLBCL is Activated B cell (ABC) DLBCL. In some embodiments, the DLBCL is Germinal center B cell-like (GCB) DLBCL.

In some embodiments, methods described herein further comprise identifying the subject as having a deceased chance of a PFS24 event (e.g., relapse, retreatment, or death) relative to other LME types when the subject is assigned type LME-C or LME-A.

In some embodiments, methods described herein further comprise identifying the subject as having an increased chance of a PFS24 event (e.g., relapse, retreatment, or death) relative to other LME types when the subject is assigned type LME-D.

In some embodiments, methods described herein further comprise obtaining an International Prognostic Index (IPI) score of the subject. In some embodiments, the IPI score is Low, Intermediate, or High.

In some embodiments, methods described herein comprise identifying the subject as having a deceased chance of a PFS24 event (e.g., relapse, retreatment, or death) relative to other LME types when the DLBCL is type LME-C ABC and the IPI score is High.

In some embodiments, methods described herein comprise identifying the subject as having an increased chance of a PFS24 event (e.g., relapse, retreatment, or death)

relative to other LME types when the DLBCL is type LME-D GCB and the IPI score is High.

In some embodiments, methods described herein comprise identifying the subject as having an increased chance of a PFS24 event (e.g., relapse, retreatment, or death) relative to other LME types when the DLBCL is type LME-A or LME-D ABC and the IPI score is Intermediate.

In some embodiments, the subject is a mammal. In some embodiments, the subject is a human.

In some embodiments, methods described herein further comprise providing a recommendation to administer one or more immunotherapeutic agents to the subject. In some embodiments, the immunotherapeutic agent comprises Rituximab.

DETAILED DESCRIPTION

Figure 1A:
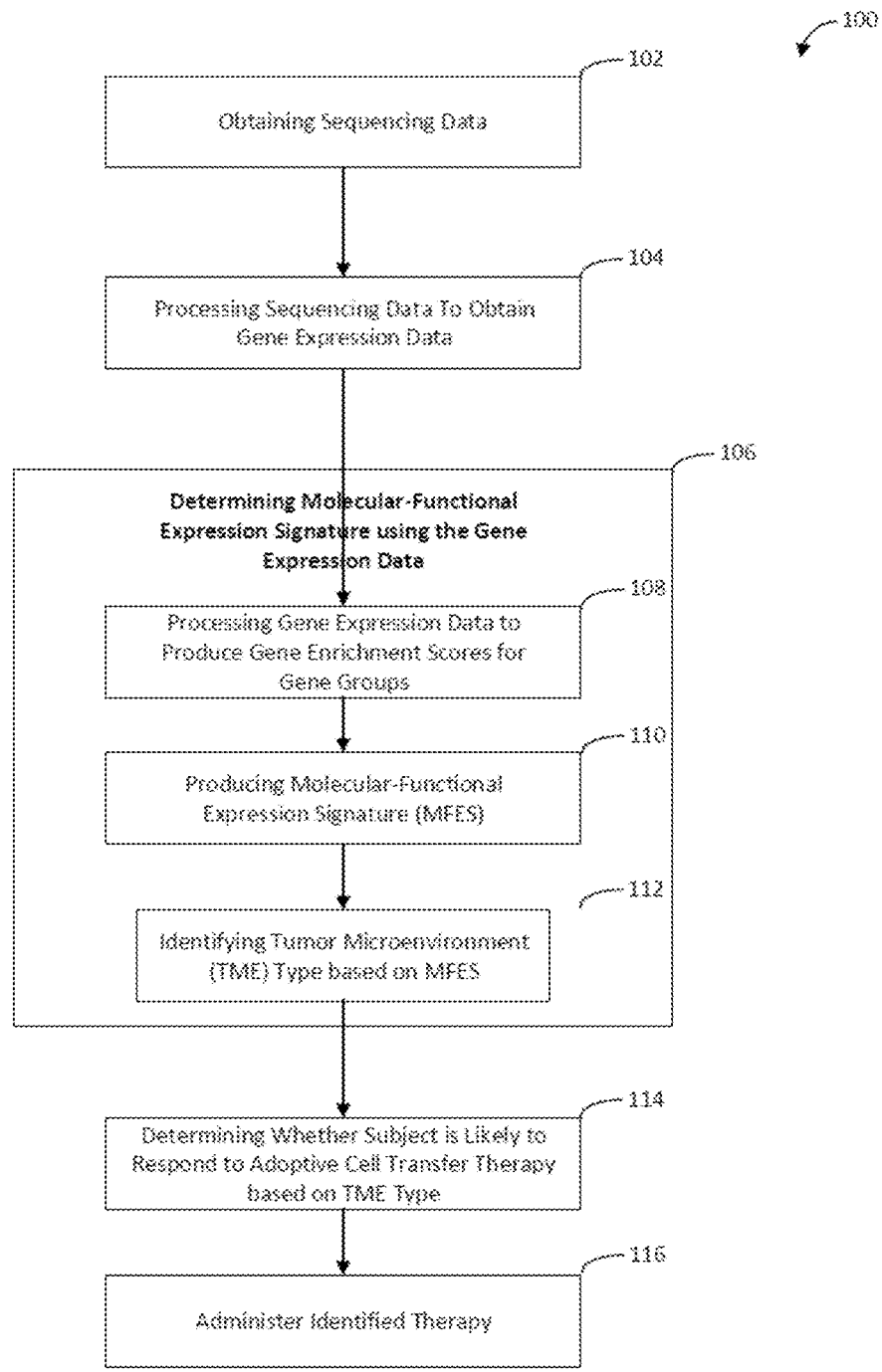
FIG. 1A provides an example of a processes for identifying the tumor microenvironment (TME) type of a subject, according to some aspects of the invention. In some embodiments, the process includes obtaining sequencing data from a biological sample obtained from a subject, processing the sequencing data to obtain gene expression data, processing the gene expression data to obtain gene enrichment scores for gene groups, producing a molecular-functional expression signature (MFES), identifying a TME type based on the MFES, and determining whether or not a subject is likely to respond to an adoptive cell transfer therapy based on the TME type. In some embodiments, the method comprises normalizing the MFES to the MFES of a cohort of samples with similar cancer diagnosis (e.g., solid tumor), the protocol of which are described in U.S. Pat. No. 10,311,967, the entire contents of which are incorporated herein by reference. In some embodiments, the method further comprises administering an identified therapy (e.g., an adoptive cell transfer therapy, such as CAR-T therapy) to the subject.

Aspects of the disclosure relate to compositions and methods for determining whether or not a subject is likely to respond to certain adoptive cell therapies (e.g., chimeric antigen receptor (CAR) T-cell therapy, etc.). In some embodiments, the methods comprise the steps of identifying a subject as having a tumor microenvironment (TME) type based upon a molecular-functional (MF) expression signature of the subject, and determining whether or not the subject is likely to respond to a chimeric antigen receptor (CAR) T-cell therapy based upon the TME type. In some embodiments, "determining whether or not a subject is likely to respond" to a CAR-T cell therapy comprises identifying the subject as a candidate for CAR-T therapy, or assisting in the identification of a subject as a candidate for CAR-T therapy.

Also described herein is a computer system comprising at least one processor; and at least one non-transitory computer readable medium containing instructions that, when executed by the at least one processor, cause the at least one processor to perform the method of any embodiment of any aspect described herein.

Also described herein is a non-transitory computer readable medium comprising instructions that, when executed by at least one processor, cause the at least one processor to perform the method of any embodiment of any aspect described herein.

In some embodiments, the methods comprise administering one or more therapeutic agents (e.g., CAR T-cell therapy, chemotherapy, radiotherapy, immunotherapy, and combinations thereof) to the subject based on the determining of TME type.

Cancer

Aspects of the disclosure relate to methods of determining the TME type of a subject having, suspected of having, or at risk of having cancer. A subject may be any mammal, for example a human, non-human primate, rodent (e.g., rat, mouse, guinea pig, etc.), dog, cat, horse etc. In some embodiments, a subject is a human.

As used herein, "cancer" refers to a disease or diseases caused by an uncontrolled division of abnormal cells in a part (or parts) of the body. Examples of cancers include but are not limited to bladder cancer, breast cancer, colon and rectal cancer, endometrial cancer, kidney cancer, leukemias, liver cancer, lung cancer, melanoma, lymphomas, pancreatic cancer, prostate cancer, thyroid Cancer, bone cancer, etc. In some embodiments, a cancer is classified as a solid tumor cancer or a blood cancer (e.g., hematological cancer). Examples of solid tumor cancers include but are not limited to sarcomas and carcinomas, glioblastomas, and melanomas. Examples of blood cancers include leukemias, such as Acute myeloid (or myelogenous) leukemia (AML), Chronic myeloid (or myelogenous) leukemia (CML), Acute lymphocytic (or lymphoblastic) leukemia (ALL), and Chronic lymphocytic leukemia (CLL), and lymphomas (which may also form solid tumors). In some embodiments, a lymphoma is a diffuse large B-cell lymphoma (DLBCL), Activated B-cell diffuse large B-cell lymphoma (ABC), or Germinal center B-cell like diffuse large B-cell lymphoma (GCB).

In some embodiments, a biological sample comprises tumor cells (e.g., cancerous tumor cells). In some embodiments, a biological sample comprises tumor cells and non-cancerous cells, for example non-cancerous tumor cells and/or cells present in the tumor microenvironment. Such a sample, in some embodiments, is referred to as a 'mixed sample'. A mixed sample of cells from a tumor can be cancer cells and non-cancerous cells including but are not limited to fibroblasts, immune cells and cells that comprise the blood vessels, proteins produced by the tumor, tumor stroma, and associated tissue cells.

In some embodiments, a subject having cancer exhibits one or more signs or symptoms of the cancer, for example, the presence of tumors, etc. In some embodiments, a subject suspected of having cancer exhibits one or more signs or symptoms of cancer, or is characterized by the presence of one or more features that predisposes the subject to cancer, for example the presence of pre-cancerous tumor cells, genetic mutations in tumor suppressor genes, etc.

In some embodiments, a biological sample is obtained from a subject for the purpose of determining a TME type. A biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue). The biological sample may be any type of sample including, for example, a sample of a bodily fluid, one or more cells, a piece of tissue, or some or all of an organ. In some embodiments, the sample may be from a cancerous tissue or organ or a tissue or organ suspected of having one or more cancerous cells. Accordingly, in some embodiments a sample is a cancer or tumor biopsy.

Biological Samples

Aspects of the disclosure relate to methods for determining whether or not a subject is likely to respond to an adoptive cell transfer therapy or determining a Diffuse Large B cell lymphoma (DLBCL) microenvironment (LME) type of a subject by obtaining sequencing data from a biological sample that has been obtained from the subject.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue). In some embodiments, the tissue sample comprises a gastrointestinal tissue sample. Examples of gastrointestinal tissue samples include but are not limited to mucosal tissue, submucosal tissue, muscular layer tissue, and serous layer tissue (also referred to as serosa tissue). In some embodiments, a gastrointestinal tissue sample comprises one or more cell types derived from a stomach (e.g., mucous cells, parietal cells, chief cells, endocrine cells, etc.). In some embodiments, a gastrointestinal tissue sample comprises one or more cell types derived from gastrointestinal tissue, for example enterocytes, Paneth cells, goblet cells, neuroendocrine cells, etc.

The biological sample may be any type of sample including, for example, a sample of a bodily fluid, one or more cells, a piece of tissue, or some or all of an organ. In some embodiments, the sample may be from a cancerous tissue or organ or a tissue or organ suspected of having one or more cancerous cells. In some embodiments, the sample may be from a healthy (e.g., non-cancerous) tissue or organ. In some embodiments, the sample from a healthy (e.g., non-cancerous) tissue or organ may be from subjects who are at risk or suspected of having the risk of developing cancer. In some embodiments, the sample from a healthy (e.g., non-cancerous) tissue or organ may be from tissues surrounding one or more cancerous cells. In some embodiments, a sample from a subject (e.g., a biopsy from a subject) may include both healthy and cancerous cells and/or tissue. In certain embodiments, one sample will be taken from a subject for analysis. In some embodiments, more than one (e.g., 2, 3, 4, 5, 6, 7, 8, 9, 10, 11, 12, 13, 14, 15, 16, 17, 18, 19, 20, or more) samples may be taken from a subject for analysis. In some embodiments, one sample from a subject will be analyzed. In certain embodiments, more than one (e.g., 2, 3, 4, 5, 6, 7, 8, 9, 10, 11, 12, 13, 14, 15, 16, 17, 18, 19, 20, or more) samples may be analyzed. If more than one sample from a subject is analyzed, the samples may be procured at the same time (e.g., more than one sample may be taken in the same procedure), or the samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure). A second or subsequent sample may be taken or obtained from the same region (e.g., from the same tumor or area of tissue) or a different region (including, e.g., a different tumor). A second or subsequent sample may be taken or obtained from the subject after one or more treatments, and may be taken from the same region or a different region. A second or subsequent sample may be taken or obtained from the subject when the first sample from the subject was taken. For example, two separate samples can be taken during the same procurement. These two separate samples can be pooled or compared for the analysis as disclosed herein. As a non-limiting example, the second or subsequent sample may be useful in determining whether the cancer in each sample has different characteristics (e.g., in the case of samples taken from two physically separate tumors in a patient) or whether the cancer has responded to one or more treatments (e.g., in the case of two or more samples from the same tumor prior to and subsequent to a treatment).

Any of the biological samples described herein may be obtained from the subject using any known technique. In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, each of the at least one biological sample is a bodily fluid sample, a cell sample, or a tissue biopsy.

Sequencing Data and Gene Expression Data

Expression data (e.g., RNA expression data and/or whole exome sequencing (WES) data) as described herein may be obtained from a variety of sources. In some embodiments, expression data may be obtained by analyzing a biological sample from a patient. In some embodiments, a biological sample is processed using a sequencing platform (e.g., DNA sequencing platform, RNA sequencing platform, exome sequencing platform, microarray sequencing platform, etc.) to produce sequencing data. In some embodiments, the sequencing data is processed to produce expression data. In some embodiments, RNA sequence data is processed by one or more bioinformatics methods or tools, for example RNA sequence quantification tools (e.g., Kallisto) and genome annotation tools (e.g., Gencode v23), in order to produce expression data. In some embodiments, microarray expression data is processed using a bioinformatics R package, such as "affy" or "limma", in order to produce expression data. In some embodiments, sequencing data and/or expression data comprises more than 5 kilobases (kb). In some embodiments, the size of the obtained RNA and/or DNA sequence data is at least 10 kb. In some embodiments, the size of the obtained RNA and/or DNA sequence data is at least 100 kb. In some embodiments, the size of the obtained RNA and/or DNA sequence data is at least 500 kb. In some embodiments, the size of the obtained RNA and/or DNA sequence data is at least 1 megabase (Mb). In some embodiments, the size of the obtained RNA and/or DNA sequence data is at least 10 Mb. In some embodiments, the size of the obtained RNA and/or DNA sequence data is at least 100 Mb. In some embodiments, the size of the obtained RNA and/or DNA sequence data is at least 500 Mb. In some embodiments, the size of the obtained RNA and/or DNA sequence data is at least 1 gigabase (Gb). In some embodiments, the size of the obtained RNA and/or DNA sequence data is at least 10 Gb. In some embodiments, the size of the obtained RNA and/or DNA sequence data is at least 100 Gb. In some embodiments, the size of the obtained RNA and/or DNA sequence data is at least 500 Gb.

Expression Data

Expression data (e.g., indicating expression levels) for a plurality of genes may be used for any of the methods described herein. The number of genes which may be examined may be up to and inclusive of all the genes of the subject. In some embodiments, expression levels may be examined for all of the genes of a subject. In some embodiments, the number of genes which may be examined may be more than all the genes of the subject. As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of non-limiting examples, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be used for any evaluation described herein. In some embodiments, at least two, at least three, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be examined for each gene group evaluation described herein. In some embodiments, up to 50 genes (e.g., up to two, up to three, up to four, up to five, up to six, up to seven, up to eight, up to nine, up to ten, up to eleven, up to twelve, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 31, up to 32, up to 33, up to 34, up to 35, up to 36, up to 37, up to 38, up to 39, up to 40, up to 41, up to 42, up to 43, up to 44, up to 45, up to 46, up to 47, up to 48, up to 49, or up to 50) gene groups may be used for any evaluation described herein.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., due to a gene duplication in a cancer patient's sample. The level of DNA in a sample from a subject having cancer may be reduced compared to the level of DNA in a sample from a subject not having cancer, e.g., a gene deletion in a cancer patient's sample.

RNA expression data, in some embodiments, refers to data for DNA (or gene) expressed in a sample, for example, sequencing data for a gene that is expressed in a patient's sample. In some embodiments, RNA expression data comprises RNA sequencing (RNAseq) data. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Without wishing to be bound by any theory, genome sequencing can be used for the purpose of DNA sequencing as disclosed herein. Any technique used in the art to sequence DNA may be used with the methods described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

In some embodiments, expression data is used to determine gene group expression levels. In some embodiments, gene group expression levels can be calculated to obtain gene expression scores. In some embodiments, gene group expression levels can be calculated to obtain gene enrichment scores. For example, in some embodiments, the gene group expression levels are calculated as a single sample gene set enrichment analysis (ssGSEA) score for the gene group for each sample independently. In some embodiments, each gene is weighted equally. Methods of performing GSEA are known in the art, for example as described by Reimand et al., Nature Protocols volume 14, pages 482-517 (2019) and Subramanian et al., Proc Natl Acad Sci USA 2005; 102(43):15545-50. In some embodiments, the GSEA is single sample Gene Set Enrichment Analysis (ssGSEA), which is further described herein in the section entitled "Molecular Functional (MF) Expression Signatures".

Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a mRNA in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Molecular Functional (MF) Expression Signatures

In some embodiments, determining the TME type of a subject (or a biological sample obtained from a subject) comprises determining a molecular functional (MF) expression signature (MFES) of the subject.

A "molecular functional expression signature (MFES)", as described herein, refers to information relating to molecular and cellular composition, and biological processes that are present within and/or surrounding the tumor. For example, the information surrounding the tumor as disclosed herein may comprise factors contributing to a tumor microenvironment as understood by a skilled person in the art. In some embodiments, biological processes comprise biological pathways that encompass the genes provided in Table 3 in the instant application as understood by a skilled person in the art. In some embodiments, biological processes comprise biological pathways that encompass the genes in any pathways that are relevant to TME.

In some embodiments, the MFES of a patient includes gene express scores for each of one or more groups of genes ("gene groups"). Thus, the information in the MFES may be generated using gene expression data (for example sequencing data, e.g., using whole exome sequencing data, RNA sequencing data, or other gene expression data) for the gene groups obtained by sequencing normal and/or tumor tissue. Examples of gene groups and techniques for determining gene group expression levels are described in International PCT Publication WO2018/231771, the entire contents of which are incorporated herein by reference. Aspects of the disclosure are based, in part, on the use of MF expression signatures to identify one or more (e.g., four) TME types in a biological sample obtained from a subject, and determining whether the subject is a candidate for CAR T-cell therapy based on the TME type that is identified.

A "gene group," as described herein, refers to a group of genes associated with related compositions and processes present within and/or surrounding a tumor. For example, Angiogenesis gene group provides information related to blood vessel system composition and activity within a tumor. Examples of information related to blood vessel system composition and activity within a tumor presented in the angiogenesis gene group include, but are not limited to, the number of blood vessels, the growth of lymphatic vessels, integrity of intercellular junctions of endothelial cells, growth of microvascular endothelial cells, and vascular remodeling.

Exemplary signatures in a MF expression signature may include, but are not limited to, Lymphatic endothelium (LEC), Angiogenesis (VEC), Cancer-associated fibroblasts (CAF), Fibroblastic reticular cells (FRC), Matrix (ECM), Matrix Remodeling (ECM remodeling), Granulocyte traffic, Protumor cytokines (IS cytokines), Follicular Dendritic Cells (FDC), Macrophages, M1 signature (activated M1), Effector cell traffic (T cell traffic), Major histocompatibility complex II (MHC-11), Major histocompatibility complex I (MHC-I), Follicular B helper T cells (TFH), Regulatory T cells (Treg), T cells (TIL), Checkpoint inhibition (IS checkpoints), Natural Killer Cells (NK cells), B cell traffic, Benign B cells (B cells), and Tumor proliferation rate (cell proliferation).

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes as shown in the following lists of gene groups. In some embodiments, the genes can include genes that across all gene groups in the following lists. In some embodiments, the genes can include genes from one or more, but not all gene groups in the following lists. In some embodiments, the genes can include genes from one gene group in the following lists. In some embodiments all of the listed genes are selected from each group. In some embodiments the numbers of genes in each selected group are not the same, and at least one gene from each gene group is selected (e.g., 1, 2, 3, 4, 5, or more genes in each gene group are selected): Lymphatic endothelium (LEC): JAM3, PPPJR13B, CXCL12, PDPN, CXADR, FLT4, CCL21, FOXC2, EDNRB, LYVE1, PROX1, SOX8, JAM2; Angiogenesis (VEC): CDH5, PGF, PDGFC, TEK, VEGFC, CXCL8, VWF, CXCR2, ANGP11, CXCL5, FLT1, VEGFA, KDR, VEGFB, ANGPT2; Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, TGFB2; Fibroblastic reticular cells (FRC): PDGFRA, ACTA2, ICAM1, NT5E, VIM, PDPN, THY1, DES, VCAM1, PTGS2, LIBR; Matrix (ECM): COL1A1, COL3A1, LGALS7, FN1, VTN, COL1A2, COL4A1; Matrix Remodeling (ECM remodeling): TIMP1, TIMP2, MMP2, MMP9, (A9; Granulocyte traffic: KITLG, CXCL8, CXCR1, CXCR2, CXCL5, KIT, CCL11, CCR3, CXCL1, CXCL2; Protumor cytokines (IS cytokines): CCL4, IL6, TNFSF13B, MIF, CXCL8, IL22, IL10; Follicular Dendritic Cells (FDC): PDPN, TNFRSFIA, LIBR, FDCSP, CLU, PRNP, BST1; Macrophages: IL10, MSR1, ARG1, CSF1R, CD163, MRC1, CSF1; M1 signature (activated M1): TNF, NOS2, IL1B, CMKLR1; Effector cell traffic (T cell traffic): CXCL11, CXCL10, CXCL9, CXCR3, CX3CL, CCL5, CX3CR1; Major histocompatibility complex 11 (MHC-II): HLA-DQB1, HLA-DPB1, HLA-DPA1, HLA-DRA, HLA-DQA1, HLA-DMA, HLA-DRB1, HLA-DMB; Major histocompatibility complex I (MHC-I): TAP1, HLA-C, B2M, HLA-B, HLA-A, TAP2; Follicular B helper T cells (TFH): CD40LG, SH2D1A, CD84, CXCR5, IL4, IL6, MAF, BCL6, IL21, ICOS; Regulatory T cells (Treg): CCR8, CTLA4, IKZF2, IKZF4, FOXP3, I10, TNFRSF18; T cells (TIL): CD3D, TRAT1, TBX21, TRBC2, ITK, CD28, CD3E, TRBC1, TRAC, CD3G; Checkpoint inhibition (IS checkpoints): CTLA4, HAVCR2, CD274, PDCD1, BTLA, TIGIT, PDCDILG2, LAG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, KLRF7; B cell traffic: CXCL13, CXCR5, CCR6, CCL20; Benign B cells (B cells): CD79B, MS4A1, STAP1, TNFRSF17, CD24, CD22, TNFRSF13B, BLK, CD19, PAX5, CD79A, TNFRSF13C, FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, BUB1.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Lymphatic endothelium (LEC): JAM3, PPP1R13B, CXCL12, PDPN, CXADR, FLT4, CCL21, FOXC2, EDNRB, LYVE1, PROX1, SOX18, JAM2.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Angiogenesis (VEC): CDH5, PGF, PDGFC, TEK, VEGFC, CXCL8, VWF, CXCR2, ANGPT1, CXCL5, FL TI, VEGFA, KDR, VEGFB, ANGPT2.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Cancer-associated fibroblasts (CAF): COL1A. MMP2, LGALS1, MMP7, LRP1, CD248, S100A4, PAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, TGFB2.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Fibroblastic reticular cells (FRC): PDGFRA, ACTA2, ICAM1, NT5E, VIM, PDPN, THY1, DES, VCAM1, PTGS2, LTBR.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Matrix (ECM): COL1A1, COL3A1, LGALS7, FN1, VTN, COL1A2, COL4AL.

In some embodiments, the gene groups of the molecular-functional (MF) expression signature may comprise at least two genes (e.g., at least two genes, at least three genes, at least four genes, at least five genes) as shown in the following lists: Matrix Remodeling (ECM remodeling): TIMP1, TIMP2, MMP2, MMP9, CA9.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes) as shown in the following lists: Granulocyte traffic: KITLG, CXCL8, CXCR1, CXCR2, CXCL5, KIT, CCL11, CCR3, CXCL1, CXCL2.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Protumor cytokines (IS cytokines): CCL4, IL6, TNFSF13B, MIF, CXCL8, IL22, IL10.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Follicular Dendritic Cells (FDC): PDPN, TNFRSFIA, LTBR, FDCSP, CLU, PRNP, BST1.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Macrophages: IL10, MSR1, ARG1, CSF1R, CD163, MRC1, CSF1.

In some embodiments, the gene groups of the molecular-functional (MF) expression signature may comprise at least two genes (e.g., at least two genes, at least three genes, at least four genes) as shown in the following lists: M1 signature (activated M1): TNF, NOS2, IL1B, CMKLR1.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Effector cell traffic (T cell traffic): CXCL11, CXCL10, CXCL9, CXCR3, CX3CL1, CCL5, CX3CR1.

In some embodiments, the gene groups of the molecular-functional (MF) expression signature may comprise at least two genes (e.g., at least two genes, at least three genes, at least four genes, at least five genes, at least six genes, at least seven genes, at least eight genes) as shown in the following lists: Major histocompatibility complex II (MHC-II): HLA-DQB1, HLA-DPB1, HLA-DPA1, HLA-DRA, HLA-DQA1, HLA-DMA, HLA-DRB1, HLA-DMB.

In some embodiments, the gene groups of the molecular-functional (MF) expression signature may comprise at least two genes (e.g., at least two genes, at least three genes, at least four genes, at least five genes, at least six genes) as shown in the following lists: Major histocompatibility complex I (MHC-I): TAP1, HLA-C, B2M, HLA-B, HLA-A, TAP2.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Follicular B helper T cells (TFH): CD40LG, SH2D1A, CD84, CXCR5, IL4, IL6, MAF, BCL6, IL21, ICOS.

In some embodiments, the gene groups of the molecular-functional (MF) expression signature may comprise at least two genes (e.g., at least two genes, at least three genes, at least four genes, at least five genes, at least six genes, at least seven genes) as shown in the following lists: Regulatory T cells (Treg): (CR8, CTLA4, IKZF2, IKZF4, FOXP3, IL10, TNFRSF18.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes) as shown in the following lists: T cells (TIL): CD3D, TRAT1, TBX21, TRBC2, ITK, CD28, CD3E, TRBC1, TRAC, CD3G.

In some embodiments, the gene groups of the molecular-functional (MF) expression signature may comprise at least two genes (e.g., at least two genes, at least three genes, at least four genes, at least five genes, at least six genes, at least seven genes, at least eight genes) as shown in the following lists: Checkpoint inhibition (IS checkpoints): CTLA4, HAVCR2, CD274, PDCD1, BTLA, TIGIT, PDCD1LG2, LAG3.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, KLRF1.

In some embodiments, the gene groups of the molecular-functional (MF) expression signature may comprise at least two genes (e.g., at least two genes, at least three genes, at least four genes) as shown in the following lists: B cell traffic: CXCL13, CXCR5, CCR6, CCL20.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Benign B cells (B cells): CD79B, MS4A1, STAP1, TNFRSF17, CD24, CD22, TNFRSF13B, BLK, CD19, PAX5, CD79A, TNFRSF13C, FCRL5.

In some embodiments, the gene groups of the molecular-functional (MF) expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, BUB1.

In some embodiments, determining gene group expression scores for each of the genes comprises determining the gene expression data that is available. For example, the available gene expression data may include all genes in the gene sets as disclosed herein. In some embodiments, the available gene expression data may not include all genes in the gene sets as disclosed herein.

In some embodiments, a molecular-functional signature is calculated by first performing single sample Gene Set Enrichment Analysis (ssGSEA) on expression data to produce a plurality of gene group enrichment scores. Single sample GSEA (ssGSEA) is generally known in the art, for example as described by Barbie et al. Nature. 2009 Nov. 5; 462(7269): 108-112. In some embodiments, ssGSEA is performed according to the following algorithm:

$$ssGSEA \text{ score} = \frac{\sum_{i}^{N} r_i^{1.25}}{\sum_{i}^{N} r_i^{0.25}} - \frac{(M - N + 1)}{2}$$

$r_i$—rank of ith gene in expression matrix
N—number of genes in geneset
M—total number of genes in expression matrix In some embodiments, the ssGSEA is performed on expression data from a subject. In some embodiments, a molecular-functional signature is calculated by performing single sample Gene Set Enrichment Analysis (ssGSEA) on expression data from a plurality of subjects, for example expression data from one or more cohorts of subjects in order to produce a plurality of enrichment scores.

In some embodiments, ssGSEA is performed on expression data comprising three or more (e.g., 3, 4, 5, 6, 7, 8, 9, 10, 11, 12, 13, 14, 15, 16, 17, 18, 19, or 20) gene groups set forth in Table 3. In some embodiments, each of the gene groups separately comprises one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or more) genes listed in Table 3. In some embodiments, a molecular-functional signature is produced by performing ssGSEA on all 25 of the gene groups in Table 3, each gene group including all listed genes in Table 3.

In some embodiments, one or more (e.g., a plurality) of enrichment scores are normalized in order to produce a molecular-functional signature for the expression data (e.g., expression data of the subject or of a cohort of subjects). In some embodiments, the enrichment scores are normalized by median scaling. In some embodiments, median scaling comprises clipping the range of enrichment scores to about −4.0 to +4.0. In some embodiments, median scaling produces a molecular-functional signature of the subject.

The MFES of the subject may be associated with any of the tumor microenvironment (TME) type clusters or lymphoma microenvironment (LME) type clusters described herein, for example in the sections entitled "Tumor Microenvironment (TME) Types" and "Lymphoma Microenvironment (LME) Types". In some embodiments, the MFES of a subject is associated with a solid cancer TME type A cluster. In some embodiments, the MFES of a subject is associated with a solid cancer TME type B cluster. In some embodiments, the MFES of a subject is associated with a solid cancer TME type C cluster. In some embodiments, the MFES of a subject is associated with a solid cancer TME type D cluster. In some embodiments, the MFES of a subject is associated with a blood cancer TME type A cluster. In some embodiments, the MFES of a subject is associated with a blood cancer TME type B cluster. In some embodiments, the MFES of a subject is associated with a blood cancer TME type C cluster. In some embodiments, the MFES of a subject is associated with a blood cancer TME type C cluster. In some embodiments, the lymphoma microenvironment (LME) signature of a subject is associated with a lymphoma microenvironment (LME) type 1 (LME-B) cluster. In some embodiments, the LME signature of a subject is associated with a lymphoma microenvironment (LME) type 2 (LME-C) cluster. In some embodiments, the LME signature of a subject is associated with a lymphoma microenvironment (LME) type 3 (LME-A) cluster. In some embodiments, the LME signature of a subject is associated with a lymphoma microenvironment (LME) type 4 (LME-D) cluster.

A subject's MFES or LME signature may be associated with one or multiple of the TME type clusters or LME type clusters in any suitable way. For example, a MFES may be associated with one of the TME type clusters using a similarity metric (e.g., by associating the MFES with the TME type cluster whose centroid is closest to the MFES according to the similarity metric). As another example, a statistical classifier (e.g., k-means classifier or any other suitable type of statistical classifier) may be trained to classify the MFES as belonging to one or multiple of the TME type clusters.

Lymphoma Microenvironment (LME) Signatures

In some embodiments, determining the LME type of a subject (or a biological sample obtained from a subject) comprises determining a LME signature of the subject.

Exemplary LME signatures may include, but are not limited to, gene expression scores for the following gene groups: Lymphatic endothelium (LEC), Angiogenesis (VEC), Cancer-associated fibroblasts (CAF), Fibroblastic reticular cells (FRC), Matrix (ECM), Matrix Remodeling (ECM remodeling), Granulocyte traffic, Protumor cytokines (IS cytokines), Follicular Dendritic Cells (FDC), Macrophages, M1 signature (activated M1), Effector cell traffic (T cell traffic), Major histocompatibility complex II (MHC-II), Major histocompatibility complex I (MHC-I), Follicular B helper T cells (TFH), Regulatory T cells (Treg), T cells (TIL), Checkpoint inhibition (IS checkpoints), Natural Killer Cells (NK cells), B cell traffic, Benign B cells (B cells), and Tumor proliferation rate (cell proliferation). In some embodiments, a LME signature comprises one or more PROGENY pathway scores selected from the following: Nuclear factor kappa B (NFkB), Phosphoinositide 3-kinase (PI3K), and p53.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same). In some embodiments, the genes can include genes that across all gene groups in the following lists. In some embodiments, the genes can include genes from one or more, but not all gene groups in the following lists. For example, in some embodiments, the genes can include at least 75% of the genes across all gene groups in the following list. In some embodiments, the genes can include genes from one gene group in the following lists.

The lists as disclosed herein comprise: Lymphatic endothelium (LEC): JAM3, PPPJR13B, CXCL12, PDPN, CXADR, FLT4, CCL21, FOXC2, EDNRB, LYVE4, PROX1, SOX18, JAM2; Angiogenesis (VEC): CDH5, PGF, PDGFC, TEK, VEGFC, CXCL8, VWF, CXCR2, ANGPT1, CXCL5, FLT1, VEGFA, KDR, VEGFB, ANGPT2; Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, TGFB2; Fibroblastic reticular cells (FRC): PDGFRA, ACTA2, ICAM1, NT5E, VIM, PDPN, THY1, DES, VCAM1, PTGS2, LIBR; Matrix (ECM): COL1A1, COL3A1, LGALS7, FN1, VTN, COL1A2, COL4A1; Matrix Remodeling (ECM remodeling): TIMP1, TIMP2, MMP2, MMP9, CA9; Granulocyte traffic: KITLG, CXCL8, CXCR1, CXCR2, CXCL5, KIT, CCL11, CCR3, CXCL1, CXCL2; Protumor cytokines (IS cytokines): CCL4, 116, TNFSF13B, MIF, CXCL8, IL22, IL10; Follicular Dendritic Cells (FDC): PDPN, TNFRSF1A, LTBR, FDCSP, CLU, PRNP, BST; Macrophages: IL10, MSR1, ARG1, CSF1R, CD163, MRC1, CSF1; M1 signature (activated M1): TNF, NOS2, IL1B, CMKLR1; Effector cell traffic (T cell traffic): CXCL11, CXCL10, CXCL9, CXCR3, CX3CL1, CCL5, CX3CR1; Major histocompatibility complex II (MHC-II): HLA-DQB1, HLA-DPB1, HLA-DPA1, HLA-DRA, HLA-DQA1, HLA-DMA, HLA-DRB1, HLA-DMB; Major histocompatibility complex I (MHC-I): TAP1, HLA-C, B2M, HLA-B, HLA-A, TAP2; Follicular B helper T cells (TFH): CD40LG, SH2D1A, CD84, CXCR5, IL4, IL6, MAF, BCL6, IL21, ICOS; Regulatory T cells (Treg): CCR8, CTIA4, IKZF2, IKZF4, FOXP3, IL10, TNFRSF18; T cell s (TIL): CD3D, TRAT1, TBX21, TRBC2, I7K, CD28, CD3E, TRBC1, TRAC, CD3G; Checkpoint inhibition (IS checkpoints): CTLA4, HAVCR2, CD274, PDCD1, BTLA, TIGIT, PDCDILG2, LAG3; Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, KLRF1; B cell traffic:: CXCL13, CXCR5, CCR6, CCL20; Benign B cells (B cells): CD79B, MS4A1, STAP1, TNFRSF7, CD24, CD22, TNFRSF13B, BLK, CD19, PAX5, CD79A, TNFRSF13C, FCRL5; and Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, BUB1.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Lymphatic endothelium (LEC): JAM3, PPP1R13B, CXCL12, PDPN, CXADR, FLT4, CCL21, FOXC2, EDNRB, LYVE1, PROX1, SOX18, JAM2.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Angiogenesis (VEC): CDH5, PGF, PDGFC, TEK, VEGFC, CXCL8, VWF, CXCR2, ANGPT1, CXCL5, FLT1, VEGFA, KDR, VEGFB, ANGPT2.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, TGFB2.

In some embodiments, the gene groups of the LME expression signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Fibroblastic reticular cells (FRC): PDGFRA, ACTA2, ICAM1, NT5E, VIM, PDPN, THY1, DES, VCAM1, PTGS2, LTBR.

In some embodiments, the gene groups of the LME signature may comprise at least two genes (e.g., at least two genes, at least three genes, at least four genes, at least five genes, at least six genes, at least seven genes) as shown in the following lists: Matrix (ECM): COL1A1, COL3A1, LGALS7, FN1, VTN, COL1A2, COL4A1.

In some embodiments, the gene groups of the LME signature may comprise at least two genes (e.g., at least two genes, at least three genes, at least four genes, at least five genes,) as shown in the following lists: Matrix Remodeling (ECM remodeling): TIMP1, TIMP2, MMP2, MMP9, CA9.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes) as shown in the following lists: Granulocyte traffic: KITLG, CXCL8, CXCR1, CXCR2, CXCL5, KIT, CCL11, CCR3, CXCL1, CXCL2.

In some embodiments, the gene groups of the LME signature may comprise at least two genes (e.g., at least two genes, at least three genes, at least four genes, at least five genes, at least six genes, at least seven genes) as shown in the following lists: Protumor cytokines (IS cytokines): CCL4, IL6, TNFSF13B, MIF, CXCL8, IL22, IL10.

In some embodiments, the gene groups of the LME signature may comprise at least two genes (e.g., at least two genes, at least three genes, at least four genes, at least five genes, at least six genes, at least seven genes) as shown in the following lists: Follicular Dendritic Cells (FDC): PDPN, TNFRSFIA, LTBR, FDCSP, CLU, PRNP, BST1.

In some embodiments, the gene groups of the LME signature may comprise at least two genes (e.g., at least two genes, at least three genes, at least four genes, at least five genes, at least six genes, at least seven genes) as shown in the following lists: Macrophages: IL10, MSR1, ARG1, CSF1R, CD163, MRC1, CSF.

In some embodiments, the gene groups of the LME signature may comprise at least two genes (e.g., at least two genes, at least three genes, at least four genes) as shown in the following lists: M1 signature (activated M1): TNF, NOS2, IL1B, CMKLR1.

In some embodiments, the gene groups of the LME signature may comprise at least two genes (e.g., at least two genes, at least three genes, at least four genes, at least five genes, at least six genes, at least seven genes) as shown in the following lists: Effector cell traffic (T cell traffic): CXCL11, CXCL10, CXCL9, CXCR3, CX3CL1, CCL5, CX3CR1.

In some embodiments, the gene groups of the LME signature may comprise at least two genes (e.g., at least two genes, at least three genes, at least four genes, at least five genes, at least six genes, at least seven genes, at least eight genes) as shown in the following lists: Major histocompatibility complex II (MHC-II): HLA-DQB1, HLA-DPB1, HLA-DPA1, HLA-DRA, HLA-DQA1, HLA-DMA, HLA-DRB1, HLA-DMB.

In some embodiments, the gene groups of the LME signature may comprise at least two genes (e.g., at least two genes, at least three genes, at least four genes, at least five genes, at least six genes) as shown in the following lists: Major histocompatibility complex I (MHC-I): TAP1, HLA-C, B2M, HLA-B, HLA-A, TAP2.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten gene) as shown in the following lists: Follicular B helper T cells (TFH): CD40LG, SH2D1A, CD84, CXCR5, IL4, IL6, MAF, BCL6, IL21, ICOS.

In some embodiments, the gene groups of the LME signature may comprise at least two genes (e.g., at least two genes, at least three genes, at least four genes, at least five genes, at least six genes, at least seven genes) as shown in the following lists: Regulatory T cells (Treg): CCR8, CL44, IKZF2, IKZF4, FOXP3, IL10, TNFRSF18.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes) as shown in the following lists: T cells (TIL): CD3D, TRAT1, TBX21, TRBC2, ITK, CD28, CD3E, TRBC1, TRAC, CD3G.

In some embodiments, the gene groups of the LME signature may comprise at least two genes (e.g., at least two genes, at least three genes, at least four genes, at least five genes, at least six genes, at least seven genes, at least eight genes) as shown in the following lists: Checkpoint inhibition (IS checkpoints): CTLA4, HAVCR2, CD274, PDCD1, BTLA, TIGIT, PDCDILG2, LAG3.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, KLRF1.

In some embodiments, the gene groups of the LME signature may comprise at least two genes (e.g., at least two genes, at least three genes, at least four genes) as shown in the following lists: B cell traffic: CXCL13, CXCR5, CCR6, CCL20.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Benign B cells (B cells): CD79B, MS4A1, STAP1, TNFRSF17, CD24, CD22, TNFRSF13B, BLK, CD19, PAX5, CD79A, TNFRSF13C, FCRL5.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, BUB1.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Nuclear factor kappa B (NFkB): PROGENY pathway score.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: Phosphoinositide 3-kinase (PI3K): PROGENY pathway score.

In some embodiments, the gene groups of the LME signature may comprise at least two genes (e.g., at least two genes, at least three genes, at least four genes, at least five genes, at least six genes, at least seven genes, at least eight genes, at least nine genes, at least ten genes, or more than ten genes) as shown in the following lists: p53: PROGENY pathway score.

Tumor Microenvironment (TME) Types

The disclosure is based, in part, on the recognition that CAR T-cell therapy (or combination therapies that include CAR T-cells) is likely to be more effective (or not effective) in subjects having certain TME types than subjects having other TME types. In some embodiments, a blood cancer or lymphoma TME type is selected from type A, type B, type C, and type D.

In some embodiments, the disclosure provides determining whether the subject is likely to respond to an adoptive cell transfer therapy (e.g., CAR T-cell therapy) using the identified TME subtype. In some embodiments, the disclosure provides identifying, from among a plurality of TME types as disclosed herein, whether the subject is likely to respond to an adoptive cell transfer therapy (e.g., CAR T-cell therapy). In some embodiments, the plurality of TME types may be associated with different likelihoods of response to adoptive cell transfer therapy.

In some embodiments, a subject having a blood cancer or lymphoma type "A" is characterized by an immuno-suppressive TME. In some embodiments, a blood cancer or lymphoma type A TME comprises macrophages that suppress T-cell function and/or a high percentage (e.g., relative to a non-tumor microenvironment or other TME types) of exhausted T-cells. In some embodiments, subject having blood cancer or lymphoma type A are expected to be resistant to treatment with CAR T-cell therapies that are not resistant to T-cell exhaustion or suppressive environments, such as CAR T-cell monotherapies (e.g., CAR T-cells that do not express any additional co-factors, such as immunomodulators or immune checkpoint inhibitors). In some embodiments, CAR T-cell therapies that are resistant to high acidosis levels are expected to be therapeutically effective in subjects having blood cancer or lymphoma TME type A. In some embodiments, combinations of CAR T-cell therapies with immune checkpoint inhibitors are expected to be therapeutically effective in subjects having blood cancer or lymphoma TME type A.

In some embodiments, a subject having a blood cancer or lymphoma type "B" is characterized by having genotypes and/or phenotypes close to normal cells. In some embodiments, a blood cancer or lymphoma type B TME is characterized by an increased number of CD4+, Follicular helper T-cells (Th), and, in certain cancers, lymphatic endothelium, relative to non-tumor microenvironments or other TME types. In some embodiments, blood cancer or lymphoma type B TME is characterized by a low tumor content and a high percentage of non-malignant B-cells. In some embodiments, blood cancer or lymphoma type B TME comprises a high percentage of HVEM, CD83, STAT6, and/or FOXO1 mutations (e.g., relative to non-tumor microenvironments or other TME types). In some embodiments, tumors or cancer cells of blood cancer or lymphoma type B are expected to respond to chemotherapy, for example Rituximab. In some embodiments, subjects having blood cancer or lymphoma type B are expected to respond to CAR-T therapy that targets cancer cell surface ligands (e.g., if CD19 is expressed on the surface then a CAR T-cell therapy targeting CD19 is expected to provide a therapeutic benefit). In some embodiments, blood cancer or lymphoma type B TME subjects are responsive to CAR T-cell monotherapies (e.g., CAR T-cells that do not express any additional co-factors, such as immunomodulators or immune checkpoint inhibitors).

In some embodiments, blood cancer or lymphoma type "C" is characterized by a TME enriched with fibroblasts, stromal cells, follicular dendritic and reticular cells (e.g., relative to non-tumor microenvironments or other TME types). In some embodiments, cancer cells in blood cancer or lymphoma type C are highly vascularized (e.g., relative to cancer cells in other TME types). In some embodiments, blood cancer or lymphoma type C TME is characterized by low lymphocyte and macrophage infiltration. Examples of cancers having type C TME include non-Hodgkin's lymphomas, such as Diffuse Large B cell lymphoma (DLBCL), Follicular Lymphoma (FL) and Mantle cell lymphoma (MCL). In some embodiments, subjects having blood cancer or lymphoma type C TME cancers are expected to respond to immune checkpoint inhibitors. CAR T-cell therapies administered in combination with immune checkpoint inhibitors are expected to be therapeutically effective. In some embodiments, blood cancer or lymphoma type C TME subjects are not responsive to CAR T-cell monotherapies (e.g., CAR T-cells that do not express any additional co-factors, such as immunomodulators or immune checkpoint inhibitors).

In some embodiments, blood cancer or lymphoma type "D" is characterized by an immune cell depleted TME having a low number of immune and stromal infiltrates, and a CD4/CD8 bias towards CD8+ cells. In some embodiments, blood cancer or lymphoma type D TME is characterized as having a higher tumor content and higher percentage of relapsed/refractory cases than other types. In some embodiments, tumors or cancer cells in a blood cancer or lymphoma type D TME are hypermethylated, aneuploid or polyploid, and/or comprise a high mutation load and/or a high circulating nucleic acid (CNA) load. In the context of lymphomas, examples of type D TME is found in double hit cancers, for example DHITsig+ cases. In some embodiments, CAR T-cell therapy is not expected to have a therapeutic benefit for subject having blood cancer or lymphoma type D TME because certain tumors in this TME are not dependent on B cell receptors, and NFkB intrinsically activated tumors are not expected to respond to CAR T-cell therapy. In some embodiments, CAR T-cell therapy may be expected to be effective in subjects having blood cancer or lymphoma type D cancers characterized by PI3K-dependent MYC-negative cancer cells. In some embodiments, CAR T-cell therapies may synergize with certain chemotherapies (e.g., Ibrutinib and other BTK inhibitors) in a type D TME.

In some embodiments, a solid tumor cancer TME type is selected from type A, type B, type C, and type D. In some embodiments, solid tumor cancer type A comprises an inflamed/vascularized, and/or inflamed/fibroblast enriched TME. In some embodiments, solid tumor cancer type B comprises an inflamed/non-vascularized, and/or inflamed/non-fibroblast enriched TME. In some embodiments, solid tumor cancer type C comprises a non-inflamed/vascularized, and/or non-inflamed/fibroblast enriched TME. In some embodiments, solid tumor cancer type D comprises a non-inflamed/non-vascularized, and/or non-inflamed/non-fibroblast enriched TME. In some embodiments, a solid tumor type D TME is also referred to as an "immune desert" type.

In some embodiments, an adoptive cell therapy can be used for treating a solid tumor cancer in a subject who has been determined as likely to respond to the adoptive cell therapy.

In some embodiments, an adoptive cell therapy can be used for treating a solid tumor cancer in a subject who has been determined as having a type A TME, a type B TME, or a type D TME.

In some embodiments, a therapeutic agent can be used for treating a solid tumor cancer in a subject who has been determined as unlikely to respond to the CAR T-cell therapy.

In some embodiments, a therapeutic agent can be used for treating a solid tumor cancer in a subject who has been determined as having a type C TME.

As used herein, "inflamed" refers to the level of compositions and processes related to inflammation in a cancer (e.g., a tumor). In some embodiments, inflamed cancers (e.g., tumors) are highly infiltrated by immune cells, and are highly active with regard to antigen presentation and T-cell activation.

As used herein, "vascularized" refers to the formation of blood vessels in a cancer (e.g., a tumor). In some embodiments, vascularized cancers (e.g., tumors) comprise high levels of cellular compositions and process related to blood vessel formation.

As used herein, "fibroblast enriched" refers to the level or amount of fibroblasts in a cancer (e.g., a tumor). In some embodiments, fibroblast enriched tumors comprise high levels of fibroblast cells.

In some embodiments, a solid tumor cancer (or blood or lymphoma) TME type is determined by a method described, for example in International PCT Publication WO2018/231771.

In some embodiments, methods further comprise determining whether a subject has a cancer type (e.g., a lymphoma type) selected from EZB, A53, BN2, EZB; MCD; N1; ST2 and/or MYC+, for example as described by Wright et al. *Cancer Cell.* 2020 Apr. 13; 37(4):551-568.e14.

In some embodiments, subjects that are EZB, A53, and/or MYC+ are not expected to respond to CAR T-cell therapy. Accordingly, in some embodiments, subjects that are EZB, A53, and/or MYC+ are administered a treatment that does not include a CAR-T cell therapy.

Turning to the Figures, FIG. 1A provides a description of one example of a process for using a computer hardware processor to perform a method of identifying the tumor microenvironment (TME) type of a subject, according to some aspects of the invention 100. First, sequencing data from a biological sample obtained from a subject is obtained 102. Methods of obtaining sequencing data are described throughout the specification including in the section entitled Sequencing Data and Gene Expression Data. Next, the sequencing data is processed to obtain gene expression data 104. Gene expression data is used to determine a molecular-functional expression signature (MFES) using the gene expression data for the subject 106. In some embodiments, the determining comprises processing the gene expression data to produce gene enrichment scores for gene groups (e.g., processing by single sample GSEA) 108. In some embodiments, the determining comprises processing of gene expression data to produce molecular-functional expression signatures (MFES) 110. In some embodiments, the determining comprises identifying a TME type based on MFES 112. In some embodiments, the method includes determining whether a subject is likely to respond to adoptive cell transfer therapy based on TME type 114. In some embodiments, the method comprises administering the identified therapy 116.

Employing such TME type selection techniques provides an improvement to patient selection technology. Selection of patients likely to respond to CAR-T therapy based upon TME type as described herein has several advantages. First, it provides physicians increased confidence in prescribing CAR-T therapy to certain populations of patients that may not have a high response rate to first-line therapeutics (e.g., rituximab). Furthermore, it helps the patients who are unlikely to respond well to a CAR-T therapy avoid the costs and inconvenience of receiving a CAR-T therapy, and to focus on exploring alternative treatments. Second, classification of patients by TME type may improve clinical trial design and efficiency by allowing selection of patients who are likely to respond to CAR-T therapy, and excluding subjects having TME types indicative of a lower response to CAR-T therapy.

Lymphoma Microenvironment (LME) Types

The disclosure is based, in part, on the determination of a lymphoma microenvironment (LME) type of a subject according to a LME signature of the subject. In some embodiments, the subject is a mammal. In some embodiments, the subject is a human.

B cell lymphomas are cancers that arise from cells that depend on numerous highly orchestrated interactions with immune and stromal cells. In addition, the progress of B cell lymphomas relies on interactions with the non-malignant cells and stromal elements that constitute the tumor microenvironment. DLBCL is a common type of high-grade non-Hodgkin lymphoma that develops from the abnormal B cells in the lymphatic system. In some embodiments, the DLBCL is Activated B cell (ABC) DLBCL. In some embodiments, the DLBCL is Germinal center B cell-like (GCB) DLBCL. In some cases, a subject may have a rare type of DLBCL. For example, rare types of DLBCL may include EBV-positive DLBCL not otherwise specified.

In some embodiments, LME types includes LME-A type, LME-B type, LME-C type, and LME-D type. In some embodiments, LME-A type, LME-B type, LME-C type, and LME-D type represent the lymphoma microenvironments of DLBCL. In some embodiments, DLBCL may comprise other LME types not otherwise specified.

Without wishing to be bound by any theory, the tumor microenvironment of B cell lymphomas may contain variable numbers of immune cells, stromal cells, blood vessels and extracellular matrix. In some embodiments, LME-B type of DLBCL is characterized by an "immunosuppressive" microenvironment enriched for T regulatory cells, myeloid-derived suppressor cells, $CD8^{PD1high}$, natural killer and macrophages type 2, and prevalence of genetic mechanisms of immune escape in malignant cells such as mutations in B2M and CD70. In some embodiments, malignant cells in LME-B DLBCL present high activity of NF-kB and JAK/STAT signaling pathways. Without wishing to be bound by any theory, it likely due to high frequency of co-occurring $MYD88^{L265}$ and CD79B mutations and the presence of a cytokine rich milieu including high expression of IL10, IL6 and TNFS13B.

In some embodiments, LME-C type of DLBCL is characterized by an "anti-tumor immunity" microenvironment enriched for T cells, follicular TH and follicular dendritic cells (FDC). In some embodiments, LME-C DLBCL presents the highest number of BCL2 translocations, EZH2 mutations, activation of cell motility, and chemotaxis pathways relative to other LME types. In some embodiments, lymphoma cells of LME-C DLBCL express higher levels of CCL20, CCR6 and CXCR5.

In some embodiments, LME-A type of DLBCL is characterized by a "mesenchymal" microenvironment enriched for cancer-associated fibroblasts (CAFs), reticular dendritic cells (DC), FDC, and endothelial cells. In some embodiments, lymphoma cells of LME-A type of DLBCL show higher mutations in BCR/Pi3K signaling intermediates SGK1 and GNA13 and activation of the TGFB signaling and matrix remodeling pathways. In addition, LME-A DLBCL expresses higher levels of MMP9, MMP2, TIMP1 and TIMP2 than other LME types. LME-A DLBCL also has a higher proportion of non-cellular LME component represented by the extracellular matrix (ECM).

In some embodiments, LME-D type of DLBCL is characterized by a "depleted" microenvironment with an increased proportion of lymphoma cells with mutations in MYD88, PIM1 and HLA-C, and higher genomic instability and epigenetic heterogeneity (e.g., by DNA methylation). Lymphoma cells of LME-D DLBCL show activation of Pi3K signaling and hypermethylation and low expression of the TGFB mediator SMAD1.

In some aspects, the present disclosure provides methods for determining a DLBCL microenvironment LME type of a subject comprising obtaining sequencing data for a subject having, suspected of having, or at risk of having a DLBCL. A subject having, suspected of having, or at risk of having a DLBCL can be identified or diagnosed by routine examination or review of family history, as would be understood by one of ordinary skill in the art.

In some embodiments, the sequence data, as used herein, can include but are not limited to DNA or RNA data.

In some embodiments, the methods comprise determining a LME signature for the subject using the sequencing data. In some embodiments, the LME signature can be obtained by using (i) a gene expression signature comprising a plurality of gene group expression scores for a respective plurality of gene groups; and/or (ii) one or more PROGENY pathway scores for the sequencing data, and assigning, from a plurality of LME types, an LME type to the subject using the LME signature. In some embodiments, a plurality of gene group expression scores for a respective plurality of gene groups can be obtained by obtaining a score for each of the plurality of groups and combining these into a LME expression signature. In some embodiments, the plurality of gene groups includes at least three of the gene groups from Table 3. In some embodiments, the LME signatures for the subjects comprise determining gene group expression scores for the genes identified in Table 3. The gene groups and their respective gene group genes are described in the present disclosure.

In some embodiments, the present disclosure provides a method for providing a prognosis, predicting survival or stratifying patient risk of a subject suspected of having, or at risk of having a Diffuse Large B cell lymphoma (DLBCL). In some embodiments, the method comprises determining a DLBCL microenvironment (LME) type of the subject as described herein.

In some embodiments, the PROGENY pathway scores for the sequencing data comprise NFkB, PI3K, and/or p53 signaling signatures. Without wishing to be bound by any theory, the NFkB, PI3K, and/or p53 signaling signatures are as understood by a skilled person in the art.

In some embodiments, the assigning comprises associating the LME signature of the subject with a cluster previously determined LME signatures selected from a LME-B type cluster, LME-C type cluster, LME-A type cluster, and LME-D type cluster. In some embodiments, LME signatures can be any genetic signatures identified by the Applicant or in the art.

In some embodiments, the methods further comprise identifying the subject as having a decreased chance of a PFS24 event (e.g., relapse, retreatment, or death) relative to other LME types when the subject is assigned type LME-C or LME-A. In some embodiments, "PFS24" represents progression-free survival at 24 months. PFS indicates the time from the start of evaluation to the earliest occurrence of progressive disease, relapse, or death. In some embodiments, a "decreased chance of a PFS24 event" indicates that a subject is at least 10%, 20%, 30%, 40%, 50%, 60%, 70%, 80%, 90%, or 100% less likely to experience a progression-free survival event (e.g., relapse, retreatment, or death) than another cancer patient or population of cancer patients (e.g., patients having the same cancer, such as lymphoma, but not the same LME type as the subject).

In some embodiments, the methods further comprise identifying the subject as having an increased chance of a PFS24 event (e.g., relapse, retreatment, or death) relative to other LME types when the subject is assigned type LME-D. In some embodiments, an "increased chance of a PFS24 event" indicates that a subject is at least 10%, 20%, 30%, 40%, 50%, 60%, 70%, 80%, 90%, or 100% more likely to experience a progression-free survival event (e.g., relapse, retreatment, or death) than another cancer patient or population of cancer patients (e.g., patients having the same cancer, such as lymphoma, but not the same LME type as the subject).

In some embodiments, the methods further comprise obtaining an International Prognostic Index (IPI) score of the subject. In some embodiments, the IPI is a score designated for the subjects who may have non-Hodgkin's lymphoma. The IPI is used for predicting outcomes in patients with aggressive non-Hodgkin's lymphoma on the basis of the subjects' clinical characteristics before treatment. In some embodiments, the IPI score is Low, Intermediate, or High. In some embodiments, the classification of the IPI score can depend on the number of risk factors.

In some embodiments, the methods further comprise identifying the subject as having a decreased chance of a PFS24 event (e.g., relapse, retreatment, or death) relative to other LME types when the DLBCL is type LME-C ABC and the IPI score is High. In some embodiments, the methods further comprise identifying the subject as having an increased chance of a PFS24 event (e.g., relapse, retreatment, or death) relative to other LME types when the DLBCL is type LME-D GCB and the IPI score is High. In some embodiments, the methods further comprise identifying the subject as having an increased chance of a PFS24 event (e.g., relapse, retreatment, or death) relative to other LME types when the DLBCL is type LME-A or LME-D ABC and the IPI score is Intermediate.

In some embodiments, the methods further comprise providing a recommendation to administer one or more immunotherapeutic agents to the subject. In some embodiments, the one or more immunotherapeutic agents comprises Rituximab.

In some embodiments, the methods described herein comprise the use of at least one computer hardware processor to perform the determination.

In some aspects, the present disclosure provides methods for treating a subject having Diffuse Large B cell lymphoma (DLBCL). In some embodiments, the method comprises administering to a subject having been identified as having DLBCL characterized by a type LME-C or type LME-A one or more immunotherapeutic agents. In some embodiments, the one or more immunotherapeutic agents include any immunotherapeutic agents as disclosed herein.

In some embodiments, the subject has been identified as having a type LME-C or type LME-A by a method comprising: using at least one computer hardware processor to perform: obtaining sequencing data for a subject having, suspected of having, or at risk of having a DLBCL. The methods comprise determining a LME signature for the subject using the sequencing data, wherein the LME signature is obtained using: (i) a gene expression signature comprising a plurality of gene group expression scores for a respective plurality of gene groups; and/or (ii) one or more PROGENY pathway scores for the sequencing data. In some embodiments, the methods comprise assigning, from a plurality of LME types, an LME type to the subject using the LME signature. In some embodiments, a plurality of gene group expression scores for a respective plurality of gene groups can be obtained by obtaining a score for each of the plurality of groups and combining these into a LME expression signature.

Figure 1B:
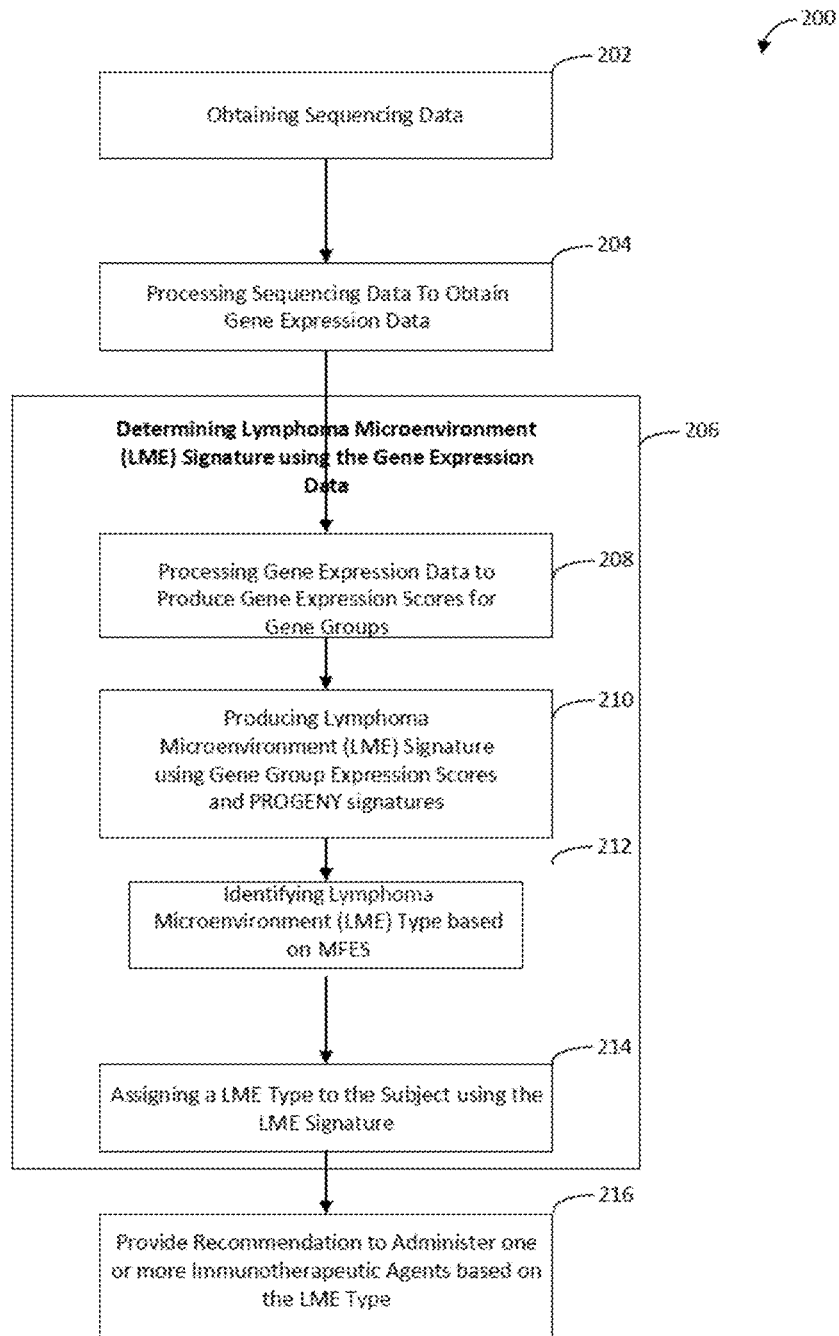
FIG. 1B provides an example of a processes for identifying the lymphoma microenvironment (LME) type of a subject, according to some aspects of the invention. In some embodiments, the process includes obtaining sequencing data from a biological sample obtained from a subject, processing the sequencing data to obtain gene expression data, processing the gene expression data to obtain gene enrichment scores for gene groups and PROGENY pathway scores, producing a lymphoma microenvironment (LME) signature, and identifying a LME type based on the LME signature. In some embodiments, the method further comprises providing a recommendation to administer one or more immunotherapeutic agents based on the LME type.

FIG. 1B provides a description of one example of a process for using a computer hardware processor to perform a method of identifying the lymphoma microenvironment (LME) type of a subject, according to some aspects of the invention 200. First, sequencing data from a biological sample obtained from a subject is obtained 202. Methods of obtaining sequencing data are described throughout the specification including in the section entitled Sequencing Data and Gene Expression Data. Next, the sequencing data is processed to obtain gene expression data 204. Gene expression data is used to determine a lymphoma microenvironment signature for the subject 206. In some embodiments, the determining comprises processing the gene expression data to produce gene expression scores for gene groups 208. In some embodiments, processing of gene expression data to produce lymphoma microenvironment signature comprises using Gene Group Expression Scores and PROGENY pathway scores on one or more gene groups, for example the gene groups listed in Table 3 210. In some embodiments, the determining comprises identifying LME types 212. In some embodiments, the method assigning a LME type to the subject using the identified LME signature 214. In some embodiments, the method comprises providing recommendation to administer one or more immunotherapeutic agents based on the LME type 216.

Employing such LME type selection techniques provides an improvement to patient categorization technology. Categorizing patients based upon LME type as described herein has several advantages. First, it provides physicians increased confidence in providing a prognosis (e.g., as relates to PFS24) or recommending particular therapeutic agents to certain populations of patients that may not otherwise identifiable. Second, classification of patients by LME type may improve clinical trial design and efficiency by allowing selection of patients who are likely to respond to therapeutic interventions, and excluding subjects having LME types indicative of a lower response to therapeutic intervention.

Combination Approach

In some aspects, methods disclosed herein may comprise determining a tumor microenvironment (TME) type and a Diffuse Large B cell lymphoma (DLBCL) microenvironment (LME) type of a subject. The disclosure is based, in part, on the determination of a lymphoma microenvironment (LME) type of a subject according to a LME signature of the subject and the determination of a TME type of a subject (or a biological sample obtained from a subject).

In some embodiments, the determination of a TME type comprises determining a molecular functional (MF) expression signature (MFES) of the subject. In some embodiments, determining the LME type of a subject (or a biological sample obtained from a subject) comprises determining a LME signature of the subject.

In some embodiments, the methods disclosed herein comprise using at least one computer hardware processor to obtaining sequencing data for a subject having, suspected of having, or at risk of having a solid tumor cancer, a blood cancer, and/or a DLBCL. In some embodiments, the subject may have more than one type of cancer. In some embodiments, the methods comprise determining a molecular-functional (MF) expression signature and a LME signature for the subject using the sequencing data. In some embodiments, the methods comprise identifying, from among tumor microenvironment (TME) types, a TME type associated with the cancer using the determined MF expression signature for the subject and obtaining the LME signature. In some embodiments, the LME signature can be obtained by using (i) a gene expression signature comprising a plurality of gene group expression scores for a respective plurality of gene groups; and/or (ii) one or more PROGENY pathway scores for the sequencing data; and assigning, from a plurality of LME types, an LME type to the subject using the LME signature.

In some embodiments, the methods disclosed herein comprise determining whether the subject is likely to respond to an adoptive cell transfer therapy based on the identified TME type. In some embodiments, the methods disclosed herein comprise determining a prognosis based at least in part on the identified LME type, and providing a recommendation for the administration of an immunotherapeutic agent. In some embodiments, the identified LME types in a subject may determine whether the subject is likely to respond to an adoptive cell transfer therapy.

In some embodiments, the methods disclosed herein comprise treating a subject having Diffuse Large B cell lymphoma (DLBCL) or other types of blood cancer.

In some embodiments, the tumor microenvironment (TME) types and the Diffuse Large B cell lymphoma (DLBCL) microenvironment (LME) types are disclosed herein.

In some embodiments, the subject is a mammal. In some embodiments, the subject is a human.

Reports

In some aspects, methods disclosed herein comprise generating a report for assisting with the preparation of recommendation for treatment. The generated report can provide summary of information, so that the administer can identify suitable therapy. The report as described herein may be a paper report, an electronic record, or a report in any format that is deemed suitable in the art. The report may be shown and/or stored on a computing device known in the art (e.g., handheld device, desktop computer, smart device, website, etc.). The report may be shown and/or stored on any device that is suitable as understood by a skilled person in the art.

In some embodiments, methods disclosed herein can be used for commercial diagnostic purposes. For example, the generated report may include but is limited to information concerning expression levels of one or more genes from any of the gene groups described herein, clinical and pathologic factors, patient's prognostic analysis, predicted response to the treatment, classification of the tumor environment or lymphoma environment, the alternative treatment recommendation, and/or other information. In some embodiments, the methods and reports may include database management for the keeping of the generated reports. For instance, the methods as disclosed herein can create a record in a database for the subject (e.g., subject 1, subject 2, etc.) and populate the specific record with data for the subject. In some embodiments, the generated report can be provided to the subject and/or to the clinicians. In some embodiments, a network connection can be established to a server computer that includes the data and report for receiving or outputting. In some embodiments, the receiving and outputting of the date or report can be requested from the server computer.

Therapeutic Methods

Molecular-functional (MF) expression signatures (MFES), in some embodiments, provide information relating to patient treatment. In some embodiments, molecular-functional (MF) expression signature provides information relating to an expected treatment outcome of a therapy. In some embodiments, the molecular-functional (MF) expression signature indicates that a specific treatment option is recommended. In some embodiments, the molecular-functional (MF) expression signature indicates that a specific treatment option is non-curative. In some embodiments, the molecular-functional (MF) expression signature indicates that a specific treatment option is dependent on a certain feature of a tumor, for example, tumor microenvironment (TME) types of the tumor. In some embodiments, a subject is administered a therapeutic (e.g., a CAR-T therapy, chemotherapy, etc.) based upon a determination of a subject's TME type or LME type. "Based on a determination" generally refers to 1) administering a particular therapy (e.g., CAR-T therapy) to a subject if or when the subject is determined to have a particular TME type, and/or 2) not administering a particular therapy (e.g., a CAR-T therapy) to a subject if or when the subject is determined to have a particular TME type.

Aspects of the disclosure relate to methods of treating a subject having (or suspected or at risk of having) cancer based upon a determination of the TME type of the subject. In some embodiments, the methods comprise administering one or more (e.g., 1, 2, 3, 4, 5, or more) therapeutic agents to the subject. In some embodiments, the therapeutic agent (or agents) administered to the subject are selected from small molecules, peptides, nucleic acids, radioisotopes, cells (e.g., CAR T-cells, etc.), and combinations thereof. Examples of therapeutic agents include chemotherapies (e.g., cytotoxic agents, etc.), immunotherapies (e.g., immune checkpoint inhibitors, such as PD-1 inhibitors, PD-L1 inhibitors, etc.), antibodies (e.g., anti-HER2 antibodies), cellular therapies (e.g. CAR T-cell therapies), gene silencing therapies (e.g., interfering RNAs, CRISPR, etc.), antibody-drug conjugates (ADCs), and combinations thereof.

In some embodiments, a subject is administered an effective amount of a therapeutic agent. "An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages for an anti-cancer therapeutic agent as described herein may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., tumor microenvironment, tumor formation, tumor growth, or cancer or tumor microenvironment (TME) types A-D, lymphoma microenvironment (LME) types LME1-LME4, etc.) may be analyzed.

Generally, for administration of any of the anti-cancer antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks: or once every month, every 2 months, or every 3 months, or longer. The progress of this therapy may be monitored by conventional techniques and assays and/or by monitoring tumor microenvironment (TME) types A-D, or lymphoma microenvironment (LME) types 1-4, as described herein. The dosing regimen (including the therapeutic used) may vary over time.

When the anti-cancer therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer.

Alleviating a cancer includes delaying the development or progression of the disease, or reducing disease severity. Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively, or in addition to the clinical techniques known in the art, development of the disease may be detectable and assessed based on other criteria. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, a PD-1 inhibitor or a PD-L1 inhibitor, a CTLA-4 inhibitor, adoptive cell transfer, therapeutic cancer vaccines, oncolytic virus therapy, T-cell therapy, and immune checkpoint inhibitors.

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine. Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); Streptomyces family antibiotics (e.g., Bleomycin, Mitomycin C, Actinomycin, and Plicamycin); and ultraviolet light.

Chimeric Antigen Receptor (CAR) Therapy

Aspects of the disclosure relate to the recognition that the TME type of a subject having (or suspected or at risk of having) cancer may be indicative of the likelihood that the subject will respond positively to CAR T-cell therapy.

Generally, a CAR is designed for a T-cell and is a chimera of a signaling domain of the T-cell receptor (TcR) complex and an antigen-recognizing domain (e.g., a single chain fragment (scFv) of an antibody) (Enblad et al., *Human Gene Therapy.* 2015; 26(8):498-505).

In some embodiments, an antigen binding receptor is a chimeric antigen receptor (CAR). A T cell that expressed a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad el al., *Human Gene Therapy.* 2015; 26(8):498-505).

There are four generations of CARs, each of which contains different components. First generation CARs join an antibody-derived scFv to the CD3zeta (ξ or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-ξ chain. Third-generation costimulatory domains may include, e.g., a combination of CD3z, CD27, CD28, 4-1BB, ICOS, or OX40. CARs, in some embodiments, contain an ectodomain (e.g., CD3ξ), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., *Blood.* 2015; 125(26):4017-4023; Kakarla and Gottschalk, *Cancer J.* 2014; 20(2):151-155).

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3ξ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., *Human Gene Therapy.* 2015; 26(8):498-505; Chmielewski and Hinrich, *Expert Opinion on Biological Therapy.* 2015; 15(8): 1145-1154.

In some embodiments, a chimeric antigen receptor is a first-generation CAR. In some embodiments, a chimeric antigen receptor is a second-generation CAR. In some embodiments, a chimeric antigen receptor is a third generation CAR. In some embodiments, the chimeric antigen receptor is a fourth generation CAR, or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. Examples of antigen binding domain targets (e.g., antigens) include but are not limited to mesothelin, EGFRvIII, TSHR, CD19, CD123, CD22, CD20, CD30, CD171, CS-1, CLL-1, CD33, GD2, GD3, BCMA, Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, Folate receptor alpha (FRa), ERBB2 (Her2/neu), MUCI, epidermal growth factor receptor (EGFR), NCAM, Prostase, PAP, ELF2M, Ephrin B2, IGF-I receptor, CAIX, LMP2, gpl00, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGEI, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYPIB 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In some embodiments, CAR is specific for an epithelial cancer cell-specific antigen (e.g., mesothelin, EGFRvIII, PSMA, ROR1, FLT3, FAP, etc. In some embodiments, a CAR is specific for a lymphoma cancer cell-specific antigen (e.g., CD19, CD20, BCMA, etc.).

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (mAbs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z el al. *Molecular Therapy Nucleic Acids* 2013; 2:e105, incorporated herein by reference). Thus, methods, in some embodiments, comprise delivering to a tumor an engineered nucleic acid that encode an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. *Sci. Transl. Med.* published online Dec. 11, 2013, incorporated herein by reference). iCARs contain an antigen-specific inhibitory receptor, for example, to block nonspecific immunosuppression, which may result from extratumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR comprises a transmembrane domain. Examples of CAR transmembrane domains include but are not limited to CD28, CD3 epsilon, CD45, CD4, CD5, CD8, CD9, CD16, CD22, CD33, CD37, CD64, CD80, CD86, CD134, CD137 and CD154.

In some embodiments, a CAR comprises an intracellular signaling domain. Examples of CAR intracellular signaling domains include but are not limited to MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAMI, CRT AM, Ly9(CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19, and CD3(, Fc receptor gamma signaling domain.

In some embodiments, as an example of the disclosure disclosed herein, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., *Cytotherapy.* 2003; 5(3): 211-226; Maude et al., *Blood.* 2015: 125(26): 4017-4023, each of which is incorporated herein by reference). In some embodiments, a CAR is expressed by a T-cell. In some embodiments, a CAR is expressed by a regulatory T-cell (e.g., a CAR T-reg).

As disclosed herein, in some embodiments, the adoptive cell transfer therapy is a CAR-T cell therapy. In some embodiments, the CAR-T cell therapy described in this application is administered at a dose of about $0.2 \times 10^6$, about $0.3 \times 10^6$, about $0.4 \times 10^6$, about $0.5 \times 10^6$, about $0.6 \times 10^6$, about $0.7 \times 10^6$, about $0.8 \times 10^6$, about $0.9 \times 10^6$, about $1 \times 10^6$, about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, about $10 \times 10^6$, about $11 \times 10^6$, about $12 \times 10^6$, about $13 \times 10^6$, about $14 \times 10^6$, about $15 \times 10^6$ CAR-positive viable T cells per Kg body weight, inclusive of all ranges and subranges therebetween, to a subject in need thereof.

In some embodiments, the CAR-T cell therapy described in this application is administered at a dose of about $0.2 \times 10^6$, about $0.3 \times 10^6$, about $0.4 \times 10^6$, about $0.5 \times 10^6$, about $0.6 \times 10^6$, about $0.7 \times 10^6$, about $0.8 \times 10^6$, about $0.9 \times 10^6$, about $1 \times 10^6$, about $2 \times 10^6$, about $3 \times 10^6$, about $4 \times 10^6$, about $5 \times 10^6$, CAR-positive viable T cells per Kg body weight, inclusive of all ranges and subranges therebetween, to a child or to a young adult who is up to 25 years old.

In some embodiments, the CAR-T cell therapy described in this application is administered at a dose of about $1 \times 10^7$, about $2 \times 10^7$, about $3 \times 10^7$, about $4 \times 10^7$, about $5 \times 10^7$, CAR-positive viable T cells per Kg body weight, inclusive of all ranges and subranges therebetween, to a subject in need thereof. In some embodiments, the CAR-T cell therapy described in this application is administered at a dose of about $0.6 \times 10^8$, about $0.7 \times 10^8$, about $0.8 \times 10^8$, about $0.9 \times 10^8$, about $1 \times 10^8$, about $2 \times 10^8$, about $3 \times 10^8$, about $4 \times 10^8$, about $5 \times 10^8$, about $6 \times 10^8$, CAR-positive viable T cells per Kg body weight, inclusive of all ranges and subranges therebetween, to a subject in need thereof. In some embodiments, the subject in need thereof is an adult who is more than 25 years old.

In some embodiments, the CAR-T cell therapy described in this application is administered at a dose of about $1 \times 10^9$, about $2 \times 10^9$, about $3 \times 10^9$, about $4 \times 10^9$, about $5 \times 10^9$, CAR-positive viable T cells per Kg body weight, inclusive of all ranges and subranges therebetween, to a subject in need thereof. In some embodiments, the CAR-T cell therapy described in this application is administered at a dose of about $1 \times 10^{10}$, about $2 \times 10^{10}$, about $3 \times 10^{10}$, CAR-positive viable T cells per Kg body weight, inclusive of all ranges and subranges therebetween, to a subject in need thereof.

In some embodiments, the CAR-T cell therapy described in this application is administered at one dose, two doses, three doses, four doses, five doses, six doses, seven doses, eight doses, nine doses, ten doses, to a subject in need thereof. In some embodiments, the CAR-T cell therapy described in this application is administered at any doses to a subject in need thereof according to the instructions by health professionals.

In some embodiments, the CAR-T cell therapy described in this application is administered at a dose of about $50 \times 10^6$, about $51 \times 10^6$, about $52 \times 10^6$, about $53 \times 10^6$, about $54 \times 10^6$, about $55 \times 10^6$, about $56 \times 10^6$, about $57 \times 10^6$, about $58 \times 10^6$, about $59 \times 10^6$, about $60 \times 10^6$, about $61 \times 10^6$, about $62 \times 10^6$, about $63 \times 10^6$, about $64 \times 10^6$, about $65 \times 10^6$, about $66 \times 10^6$, about $67 \times 10^6$, about $68 \times 10^6$, about $69 \times 10^6$, about $70 \times 10^6$, about 71×10$^6$, about 72×10$^6$, about 73×10$^6$, about 74×10$^6$, about 75×10$^6$, about 76×10$^6$, about 77×10$^6$, about 78×10$^6$, about 79×10$^6$, about 80×10$^6$, about 81×10$^6$, about 82×10$^6$, about 83×10$^6$, about 84×10$^6$, about 85×10$^6$, about 86×10$^6$, about 87×10$^6$, about 88×10$^6$, about 89×10$^6$, about 90×10$^6$, about 91×10$^6$, about 92×10$^6$, about 93×10$^6$, about 94×10$^6$, about 95×10$^6$, about 96×10$^6$, about 97×10$^6$, about 98×10$^6$, about 99×10$^6$, about 100×10$^6$, about 101×10$^6$, about 102×10$^6$, about 103×10$^6$, about 104×10$^6$, about 105×10$^6$, about 106×10$^6$, about 107×10$^6$, about 108×10$^6$, about 109×10$^6$, about 110×10$^6$, CAR-positive viable T cells, inclusive of all ranges and subranges therebetween, to a subject in need thereof.

In some embodiments, the CAR-T cell therapy described in this application is administered at a dose of about 300×10$^6$, about 301×10$^6$, about 302×10$^6$, about 303×10$^6$, about 304×10$^6$, about 305×10$^6$, about 306×10$^6$, about 307×10$^6$, about 308×10$^6$, about 309×10$^6$, about 310×10$^6$, about 311×10$^6$, about 312×10$^6$, about 313×10$^6$, about 314×10$^6$, about 315×10$^6$, about 316×10$^6$, about 317×10$^6$, about 318×10$^6$, about 319×10$^6$, about 320×10$^6$, about 321×10$^6$, about 322×10$^6$, about 323×10$^6$, about 324×10$^6$, about 325×10$^6$, about 326×10$^6$, about 327×10$^6$, about 328×10$^6$, about 329×10$^6$, about 330×10$^6$, about 331×10$^6$, about 332×10$^6$, about 333×10$^6$, about 334×10$^6$, about 335×10$^6$, about 336×10$^6$, about 337×10$^6$, about 338×10$^6$, about 339×10$^6$, about 340×10$^6$, about 341×10$^6$, about 342×10$^6$, about 343×10$^6$, about 344×10$^6$, about 345×10$^6$, about 346×10$^6$, about 347×10$^6$, about 348×10$^6$, about 349×10$^6$, about 350×10$^6$, about 351×10$^6$, about 352×10$^6$, about 353×10$^6$, about 354×10$^6$, about 355×10$^6$, about 356×10$^6$, about 357×10$^6$, about 358×10$^6$, about 359×10$^6$, about 360×10$^6$, about 361×10$^6$, about 362×10$^6$, about 363×10$^6$, about 364×10$^6$, about 365×10$^6$, about 366×10$^6$, about 367×10$^6$, about 368×10$^6$, about 369×10$^6$, about 370×10$^6$, about 371×10$^6$, about 372×10$^6$, about 373×10$^6$, about 374×10$^6$, about 375×10$^6$, about 376×10$^6$, about 377×10$^6$, about 378×10$^6$, about 379×10$^6$, about 380×10$^6$, about 381×10$^6$, about 382×10$^6$, about 383×10$^6$, about 384×10$^6$, about 385×10$^6$, about 386×10$^6$, about 387×10$^6$, about 388×10$^6$, about 389×10$^6$, about 390×10$^6$, about 391×10$^6$, about 392×10$^6$, about 393×10$^6$, about 394×10$^6$, about 395×10$^6$, about 396×10$^6$, about 397×10$^6$, about 398×10$^6$, about 399×10$^6$, about 400×10$^6$, about 401×10$^6$, about 402×10$^6$, about 403×10$^6$, about 404×10$^6$, about 405×10$^6$, about 406×10$^6$, about 407×10$^6$, about 408×10$^6$, about 409×10$^6$, about 410×10$^6$, about 411×10$^6$, about 412×10$^6$, about 413×10$^6$, about 414×10$^6$, about 415×10$^6$, about 416×10$^6$, about 417×10$^6$, about 418×10$^6$, about 419×10$^6$, about 420×10$^6$, about 421×10$^6$, about 422×10$^6$, about 423×10$^6$, about 424×10$^6$, about 425×10$^6$, about 426×10$^6$, about 427×10$^6$, about 428×10$^6$, about 429×10$^6$, about 430×10$^6$, about 431×10$^6$, about 432×10$^6$, about 433×10$^6$, about 434×10$^6$, about 435×10$^6$, about 436×10$^6$, about 437×10$^6$, about 438×10$^6$, about 439×10$^6$, about 440×10$^6$, about 441×10$^6$, about 442×10$^6$, about 443×10$^6$, about 444×10$^6$, about 445×10$^6$, about 446×10$^6$, about 447×10$^6$, about 448×10$^6$, about 449×10$^6$, about 450×10$^6$, about 451×10$^6$, about 452×10$^6$, about 453×10$^6$, about 454×10$^6$, about 455×10$^6$, about 456×10$^6$, about 457×10$^6$, about 458×10$^6$, about 459×10$^6$, about 460×10$^6$, CAR-positive viable T cells, inclusive of all ranges and subranges therebetween, to a subject in need thereof.

In some embodiments, the administration of the adoptive cell transfer therapy to a subject in need thereof is intravenous. In some embodiments, the administration of the adoptive cell transfer therapy to a subject in need thereof is intramuscular. In some embodiments, the administration of the adoptive cell transfer therapy to a subject in need thereof is any route that is suitable for the therapy.

In some embodiments, the CAR-T cell therapy described in this application is BREYANZI® (lisocabtagene maraleucel). In some embodiments, the CAR-T cell therapy described in this application is TECARTUS™ (brexucabtagene autoleucel). In some embodiments, the CAR-T cell therapy described in this application is KYMRIAH™ (tisagenlecleucel). In some embodiments, the CAR-T cell therapy described in this application is YESCARTA™ (axicabtagene ciloleucel). In some embodiments, the CAR-T cell therapy described in this application is ABECMA® (idecabtagene vicleucel). In some embodiments, the CAR-T cell therapy described in this application can be any therapy that is suitable as understood by a skilled person in the art.

In some embodiments, the CAR-T cell therapy described in this application is AUTO3 (CD19/22 CAR T cells). In some embodiments, the CAR-T cell therapy described in this application is CART-19. In some embodiments, the CAR-T cell therapy described in this application is anti-B cell maturation antigen (BCMA) CAR T cells. In some embodiments, the CAR-T cell therapy described in this application is Epidermal growth factor receptor (EGFRv)III Chimeric antigen receptor (CAR) transduced PBL.

In some embodiments, a subject having a TME type that is not expected to respond to a CAR T-cell therapy (e.g., a CAR T-cell monotherapy) is treated with a combination of a CAR T-cell and one or more additional therapeutic agents. In some embodiments, the one or more additional therapeutic agents are expressed by the CAR-T cell. In some embodiments, the one or more additional therapeutic agents are administered separately from the CAR T-cell therapy. The one or more additional therapeutic agents may be delivered before, simultaneously (e.g., at the same time, for example co-administered) with, or after the CAR T-cell therapy. In some embodiments, the one or more additional therapeutic agents are each selected from Utomilumab (e.g., CD137 activators), Rituximab+Lenalidomide, Tazemetostat (e.g., EZH2 inhibitors), immune checkpoint inhibitors (e.g., PD-1 inhibitors, PD-L1 inhibitors, etc.), Selinexor (e.g., XPO1 inhibitors), TLR agonists (e.g., TLR 1, 2, 7, 9 agonists), Venetoclax (e.g., BCL2 inhibitors), Azacitidine, Ibrutinib, antiangiogenic agents, TGFBR2 inhibitors, WNT inhibitors, cytokine therapy, and personalized cancer vaccines.

EXAMPLES

Example 1

Association of CAR-T Efficacy in Dependence on TAM Types in Solid Tumor Cancer

Figure 2:
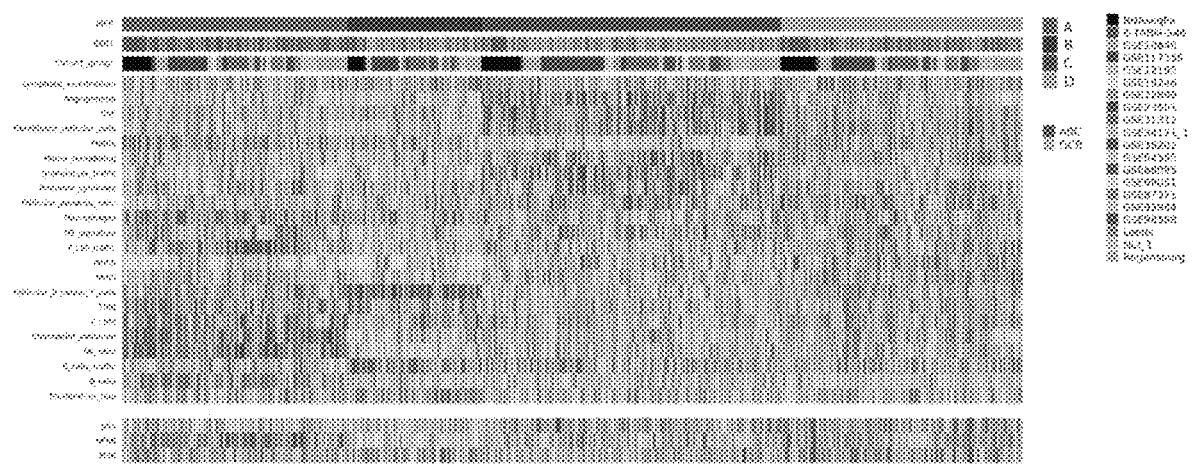
FIG. 2 shows representative gene expression data for identification of four tumor microenvironment types (A, B, C, and D), based upon molecular function profiling of cancer cells from 4244 lymphoma subjects across 20 datasets. Data shown in red represents "high." Data shown in blue represents "low." The scale of the signatures was [−2, 2].

This example describes identification of blood cancer and lymphoma or solid tumor cancer tumor microenvironment (TME) types based upon molecular function profiling of cells from biological samples (e.g., solid tumor cells and hematological cancer cells) obtained from cancer patients. FIG. 2 depicts representative data identifying four tumor microenvironment types (A, B, C, and D) from patients having lymphoma. The identification of TME types is useful, in some embodiments, for determining whether or not a patient is likely to respond positively to certain adoptive cell therapies, for example CAR T-cell therapies or combination therapies that include CAR T-cell therapies. Briefly, blood cancer and lymphoma TME types identified, and their expected response to CAR-T therapies, are described below in Table 1. Table 2 describes solid tumor cancer TME types and their expected response to CAR T-cell therapies.

The blood cancer and lymphoma type "A" is characterized by an immuno-suppressive TME. Many macrophages that suppress T-cell function are present. There is also a high percentage of exhausted T-cells. Thus, type A patients are expected to be resistant to treatment with CAR T-cell therapies that are not resistant to T-cell exhaustion or suppressive environments. CAR T-cell therapies that are resistant to high acidosis levels may also be effective. Combinations of CAR T-cell therapies with immune checkpoint inhibitors may be effective. However, type A also is characterized as having high levels of CD8+IL6 producing cells.

The blood cancer and lymphoma type "B" is characterized by having genotypes and/or phenotypes close to normal cells. Type B TME is also characterized by an increased number of CD4+, Follicular helper T-cells (Tfh), and, in certain cancers, lymphatic endothelium. Generally, type B has a low tumor content and a high percentage of non-malignant B-cells. There is also a high percentage of HVEM, CD83, STAT6, and/or FOXO1 mutations. Cells often depend on the microenvironment (e.g., Tfh cells) and rarely on intrinsic pathways. Most of the tumors of type B are expected to respond to Rituximab. Patients of this type are also expected to respond to CAR-T therapy that targets cancer cell surface ligands (e.g., if CD19 is expressed on the surface then a CAR T-cell therapy targeting CD19 is expected to provide a therapeutic benefit).

The blood cancer and lymphoma type "C" is characterized by a TME enriched with fibroblasts. Cancer cells in type C are highly vascularized. The TME is characterized by low lymphocyte and macrophage infiltration. Examples of cancers having type C TME include non-Hodgkin's lymphomas, such as DLBCL, follicular lymphoma (FL), and mantle cell lymphoma (MCL). In the TME, communication with T-cells is disrupted by B2M, CIITA Loss, EZH2 GOF; Cells in TME type C may also be characterized by PDL1 amplifications, CD70, TNFRSF9 losses. Downstream NFkB signaling is highly active through mutations in CARD11, a20, BTK, NFKBIE, MALT1, and/or TRAF2. Migratory pathways are often disrupted (e.g., G-alpha complex) by alterations in GNA13 and/or P2RY8. Type C comprises cells having a high mutation load, for example ST2 cancers or EZB type cancers. Type C TME cancers are expected to respond to immune checkpoint inhibitors, as cells frequently express high levels of PD-L1. However, high levels of IL-6 produced by the type C microenvironment (especially by non-CARs, CD8+ T-cells and Macrophages) may be associated with severe toxicity. CAR T-cell therapies administered in combination with immune checkpoint inhibitors are expected to be therapeutically effective. However, given the immunosuppressive TME of type C, CAR T-cells administered as a monotherapy are not expected to provide any therapeutic benefit.

The blood cancer and lymphoma type "D" is characterized by an immune cell depleted TME having a low number of immune and stromal infiltrates and a CD4/CD8 bias towards CD8+ cells. Type D also is characterized as having a higher tumor content and higher percentage of relapsed/refractory cases than other types. Tumors in a type D TME are typically hypermethylated, aneuploid or polyploid, with a high mutation load and circulating nucleic acid (CNA) load. In the context of lymphomas, type D has a high occurrence of double hit cancers, for example DHITsig+ cases, as well as p16 double loss, and EZB type cancers. In the type D TME, PI3K is typically more active than NFkB and a large percentage of cells comprise anti-apoptotic genes amplifications (e.g., BAK), TMEM30A mutations (e.g., B cell receptor mutations), and a high TP53 loss rate. CAR T-cell therapy is not expected to have a therapeutic benefit for type D TME because certain tumors in this TME are not dependent on B cell receptors, and NFkB intrinsically activated tumors are not expected to respond to CAR T-cell therapy. However, due to the depleted TME of type D, CAR T-cell therapy may be expected to be effective in PI3K-dependent MYC-negative cancers. Additionally, CAR T-cell therapies may synergize with certain chemotherapies (e.g., Ibrutinib and other BTK inhibitors) in a type D TME.

TABLE 1

CAR-T with TME types A-D in the context of Blood Cancer:
CAR-T target - refers to the target molecule on the surface of malignant cells, which is selected as target of CAR-T, for example CD19, CD20, etc.
Although the table includes information specific to different types of lymphoma, this example is applicable to other blood cancers, examples of which are provided herein.

| Main TME type | Additional type | Response to 1-2 gen CAR-T | Response to 3-4 gen CAR-T | Potential combinational therapy to overcome resistance or increase efficacy |
|---|---|---|---|---|
| Type-B (GCB or ABC) | CAR-T target expressed | Could be treated with CAR-T | Could be treated with CAR-T | Utomilumab (CD137 activator) Rituximab + Lenalidomide Umbralisib and other PI3K delta/gamma inhibitors |
| Type-B (GCB or ABC) | CAR-T target not expressed | Likely not responsive | Tandem CAR/ Dual Car/CAR Pooling | — |
| Type-C (GCB or ABC) | CAR-T target expressed | Likely responsive | "Armored" CARs with IL-18, IL-15, IL-12, IL-7 etc./ CARs with checkpoint blockade antibodies | Checkpoint inhibitors? |

TABLE 1-continued

CAR-T with TME types A-D in the context of Blood Cancer:
CAR-T target - refers to the target molecule on the surface of malignant cells, which is selected as target of CAR-T, for example CD19, CD20, etc.
Although the table includes information specific to different types of lymphoma, this example is applicable to other blood cancers, examples of which are provided herein.

| Main TME type | Additional type | Response to 1-2 gen CAR-T | Response to 3-4 gen CAR-T | Potential combinational therapy to overcome resistance or increase efficacy |
|---|---|---|---|---|
| Type-C (GCB or ABC) | CAR-T target not expressed | Likely not responsive | Tandem CAR/Dual Car/CAR Pooling | — |
| Type-C (GCB or ABC) | EZB or A53 or MYC+ | Likely responsive | — | Tazemetostat (EZH2 inhibitor), venetoclax (BCL2 inhibitor) |
| Type-A (GCB or ABC) | CAR-T target expressed | Likely not responsive due to immune suppression | CARs with checkpoint blockade antibodies/ CAR-T Cells with EGFRt safety system (+rituximab or cetuximab) | Checkpoint inhibitors, TLR 1, 2, 7, 9 agonists (Immunomodulators) Lenalidomide Checkpoint inhibitors |
| Type-A (GCB or ABC) | CAR-T target not expressed | Likely not responsive due to immune suppression | Tandem CAR/Dual Car/CAR Pooling | Lenalidomide |
| Type-A (GCB or ABC) | EZB or A53 or MYC+ | Likely not responsive | — | Tazemetostat (EZH2 inhibitor) |
| Type-D GCB | CAR-T target not expressed | Likely not responsive | Tandem CAR/Dual Car/CAR Pooling | Venetoclax (BCL2 inhibitors) |
| Type-D GCB | DHIT−/MYC CAR-T target expressed | May respond | — | Venetoclax (BCL2 inhibitors) |
| Type-D GCB | DHIT+/MYC+ or EZB or A53 | May respond | — | Azacitidine, Tazemetostat |
| Type-D ABC | CAR-T target expressed | May respond | — | Rituximab, Rituximab + Lenalidomide |
| Type-D ABC | CAR-T target not expressed | Likely not responsive | Tandem CAR/Dual Car/CAR Pooling | |
| Type-D ABC | MCD, TMEM30A mutants (10.1038/s41591-020-0757-z) mutants | Likely responsive to CAR-T Synergism with BKT inhibitors | —//— | Ibrutinib |
| Type-D ABC | DHIT+/MYC+ or EZB or A53 | May respond | | Azacitidine, Selinexor, Venetoclax, Tazemetostat. Ibrutinib Utomilumab (CD137 activator) |

TABLE 2

CAR-T with TME types A-D in the context of Solid Tumors (e.g., melanoma):
(CAR-T target - refers to a target molecule on the surface of malignant cells, which is selected as a target of CAR-T, for example MSLN, MAGEA3, CEA, EGFRvIII).

| Main TME type | Additional type | Response to 1-2 gen CAR-T | Response to 3-4 gen CAR-T | Potential combinational therapy to overcome resistance or increase efficacy |
|---|---|---|---|---|
| Type A (Immune Enriched, fibrotic) | CAR-T target expressed | Unknown | CAR-T cells with HPSE expression | Antiangiogenic agents TGFBR2 inhibitors |

TABLE 2-continued

CAR-T with TME types A-D in the context of Solid Tumors (e.g., melanoma):
(CAR-T target - refers to a target molecule on the surface of malignant cells, which is selected
as a target of CAR-T, for example MSLN, MAGEA3, CEA, EGFRvIII).

| Main TME type | Additional type | Response to 1-2 gen CAR-T | Response to 3-4 gen CAR-T | Potential combinational therapy to overcome resistance or increase efficacy |
|---|---|---|---|---|
| Type A (Immune Enriched, fibrotic) | CAR-T target not expressed | Potentially resistant | Tandem CAR/Dual Car/CAR Pooling | TGFBR2 inhibitors + Checkpoint inhibitors |
| Type B (Immune Enriched, non-fibrotic) | CAR-T target expressed | Potentially sensitive | CARs with checkpoint blockade antibodies | Checkpoint inhibitors |
| Type B (Immune Enriched, non-fibrotic) | CAR-T target not expressed | Potentially resistant | Tandem CAR/Dual Car/CAR Pooling | |
| Type C (Fibrotic) | CAR-T target expressed | Potentially resistant | CAR-T Cells with IL-7 and CCL19 Expression/CAR T cells with a dominant-negative TGF-βRII (dnTGF-βRII) expression/CAR-T cells with HPSE expression | TGFBR2 inhibitors WNT inhibitors (to restrain fibrosis) |
| Type C (Fibrotic) | CAR-T target not expressed | Potentially resistant | Tandem CAR/Dual Car/CAR Pooling | — |
| Type D (Immune depleted, non-fibrotic, malignant) | CAR-T target expressed | Potentially sensitive | "Armored" CARs with IL-18, IL-15, IL-12, IL-7 etc. | Cytokine therapy (IL2, IFNa) Personalized Vaccination |
| Type D (Immune depleted, non-fibrotic, malignant) | CAR-T target not expressed | Potentially resistant | Tandem CAR/Dual Car/CAR Pooling | — |

Example 2

This Example describes methods and algorithms for identification of lymphoma microenvironment (LME) types within Diffuse Large B-Cell Lymphoma (DLBCL) patients, and prognostic stratification of those patients (e.g., overall survival (OS), progression-free survival at 24 months (PFS24), etc.) based, at least in part, upon the LME type of the subject.

A large number of public DLBCL datasets (e.g., expression data, RNA-seq data, whole exome sequencing data, etc.) was collected. Roughly half of the samples in the data set have overall survival (OS) and progression-free survival (PFS) annotations and are derived from a variety of different sources. Data sets were obtained from the following publicly-available cohorts 'NCICGCI', 'NCICCR', 'GSE22898', 'Dave_BL', 'ICGC_MALY_DE', 'Regensburg', 'BAGS', 'GSE64555', 'GSE68895', 'GSE69049', 'GSE69051', 'GSE87371', 'GSE93984', 'GSE11318', 'GSE10846', 'GSE12195', 'GSE117556', 'GSE19246', 'GSE23501', 'GSE31312', 'GSE32918', 'E-TABM-346', 'GSE98588', and 'GSE38202', 'GSE34171_1'. A total of 4448 samples (2447/2001 GCB/ABC) were analyzed. Among them, 1702 patients with known PFS data (1143/559) were analyzed.

A lymphoma microenvironment (LME) type was determined for each subject based upon gene expression signatures, as described below.

In some embodiments, gene expression signatures (e.g., a signature comprising a plurality of gene group expression scores) representing the microenvironment of a DLBCL sample are calculated by single sample gene set enrichment analysis (ssGSEA) of one or more genes in one or more of the gene sets shown in Table 3. Methods of performing gene set enrichment analysis are known, for example as described by: genepattern.org/modules/docs/ssGSEAProjection/4#:~:text=Single%2Dsample%20GSEA%20(s sGSEA), down%2Dregulated%20within%20a%20sample; Subramanian et al. Gene set enrichment analysis: A knowledge-based approach for interpreting genome-wide expression profiles. PNAS. 2005; 102(43):15545-15550; and Barbie D A et al. Systematic RNA interference reveals that oncogenic KRAS-driven cancers require TBK1. Nature. 2009; 462:108-112, the entire contents of each of which are incorporated herein by reference.

In some embodiments, one or more gene expression signatures are calculated using methods described by US Patent Publication No. 2020-0273543, entitled "SYSTEMS AND METHODS FOR GENERATING, VISUALIZING AND CLASSIFYING MOLECULAR FUNCTIONAL PROFILES", the entire contents of which are incorporated herein by reference.

TABLE 3

| Gene Group | Gene Group Genes |
|---|---|
| Lymphatic endothelium (LEC) | JAM3, PPP1R13B, CXCL12, PDPN, CXADR, FLT4, CCL21, FOXC2, EDNRB, LYVE1, PROX1, SOX18, JAM2 |
| Angiogenesis (VEC) | CDH5, PGF, PDGFC, TEK, VEGFC, CXCL8, VWF, CXCR2, ANGPT1, CXCL5, FLT1, VEGFA, KDR, VEGFB, ANGPT2 |
| Cancer-associated fibroblasts (CAF) | COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, TGFB2 |
| Fibroblastic reticular cells (FRC) | PDGFRA, ACTA2, ICAM1, NT5E, VIM, PDPN, THY1, DES, VCAM1, PTGS2, LTBR |
| Matrix (ECM) | COL1A1, COL3A1, LGALS7, FN1, VTN, COL1A2, COL4A1 |
| Matrix Remodeling (ECM remodeling) | TIMP1, TIMP2, MMP2, MMP9, CA9 |
| Granulocyte traffic | KITLG,, CXCL8, CXCR1, CXCR2, CXCL5, KIT, CCL11, CCR3, CXCL1, CXCL2 |
| Protumor cytokines (IS cytokines) | CCL4, IL6, TNFSF13B, MIF, CXCL8, IL22, IL10 |
| Follicular Dendritic Cells (FDC) | PDPN, TNFRSF1A, LTBR, FDCSP, CLU, PRNP, BST1 |
| Macrophages | IL10, MSR1, ARG1, CSF1R, CD163, MRC1, CSF1 |
| M1 signature (activated M1) | TNF, NOS2, IL1B, CMKLR1, |
| Effector cell traffic (T cell traffic) | CXCL11, CXCL10, CXCL9, CXCR3, CX3CL1, CCL5, CX3CR1 |
| Major histocompatibility complex II (MHC-II) | HLA-DQB1, HLA-DPB1, HLA-DPA1, HLA-DRA, HLA-DQA1, HLA-DMA, HLA-DRB1, HLA-DMB |
| Major histocompatibility complex I (MHC-I) | TAP1, HLA-C, B2M, HLA-B, HLA-A, TAP2 |
| Follicular B helper T cells (TFH) | CD40LG, SH2D1A, CD84, CXCR5, IL4, IL6, MAF, BCL6, IL21, ICOS |
| Regulatory T cells (Treg) | CCR8, CTLA4, IKZF2, IKZF4, FOXP3, IL10, TNFRSF18 |
| T cells (TIL) | CD3D, TRAT1, TBX21, TRBC2, ITK, CD28, CD3E, TRBC1, TRAC, CD3G |
| Checkpoint inhibition (IS checkpoints) | CTLA4, HAVCR2, CD274, PDCD1, BTLA, TIGIT, PDCD1LG2, LAG3 |
| Natural Killer Cells (NK cells) | SH2D1B, GZMH, GZMB, CD160, KLRK1, NCR3, CD244, IFNG, GNLY, NCR1, CD226, NKG7, EOMES, KLRC2, FGFBP2, KIR2DL4, KLRF1 |
| B cell traffic | CXCL13, CXCR5, CCR6, CCL20 |
| Benign B cells (B cells) | CD79B, MS4A1, STAP1, TNFRSF17, CD24, CD22, TNFRSF13B, BLK, CD19, PAX5, CD79A, TNFRSF13C, FCRL5 |
| Tumor proliferation rate (cell proliferation) | MCM6, AURKB, ESCO2, CCNB1, AURKA, MKI67, CCND1, CCNE1, MCM2, MYBL2, E2F1, CETN3, CDK2, PLK1, BUB1 |
| Nuclear factor kappa B (NFkB) | PROGENY pathway score |
| Phosphoinositide 3-kinase (PI3K) | PROGENY pathway score |
| p53 | PROGENY pathway score |

After determining the gene expression signatures each sample, unsupervised clustering was performed using Leiden algorithm. Four DLBCL LME types were identified based on the clusters. Examples of LME types are described for example by Cerchietti et al. *Blood* (2019) 134 (Supplement_1): 656, the entire contents of which are incorporated herein by reference:

LME-1 DLBCL is characterized by an "immunosuppressive" microenvironment enriched for T regulatory cells, myeloid-derived suppressor cells, $CD8^{PD1high}$, natural killer and macrophages type 2, and prevalence of genetic mechanisms of immune escape in malignant cells such as mutations in B2M and CD70. Malignant cells in LME-1 DLBCL present high activity of NF-kB and JAK/STAT signaling pathways, likely due to high frequency of co-occurring $MYD88^{L265}$ and CD79B mutations and the presence of a cytokine rich milieu including high expression of IL10, IL6 and TNFS13B.

LME-2 DLBCL is characterized by an "anti-tumor immunity" microenvironment enriched for T cells, follicular $T_H$ and follicular dendritic cells (FDC), and present the highest number of BCL2 translocations and EZH2 mutations and activation of cell motility and chemotaxis pathways relative to other LME types. Lymphoma cells express higher levels of CCL20, CCR6 and CXCR5.

LME-3 DLBCL is characterized by a "mesenchymal" microenvironment enriched for cancer-associated fibroblasts (CAFs), reticular dendritic cells (DC), FDC, and endothelial cells. Lymphoma cells show higher mutations in BCR/Pi3K signaling intermediates SGK1 and GNA13 and activation of the TGFB signaling and matrix remodeling pathways. LME-3 DLBCLs express higher levels of MMP9, MMP2, TIMP1 and TIMP2 than other LME types. LME-3 DLBCL also has a higher proportion of non-cellular LME component represented by the extracellular matrix (ECM).

LME-4 DLBCL is characterized by a "depleted" microenvironment with an increased proportion of lymphoma cells with mutations in MYD88, PIM1 and HLA-C, and higher genomic instability and epigenetic heterogeneity (e.g., by DNA methylation). Lymphoma cells show activation of Pi3K signaling and hypermethylation and low expression of the TGFB mediator SMAD1.

Figure 3:
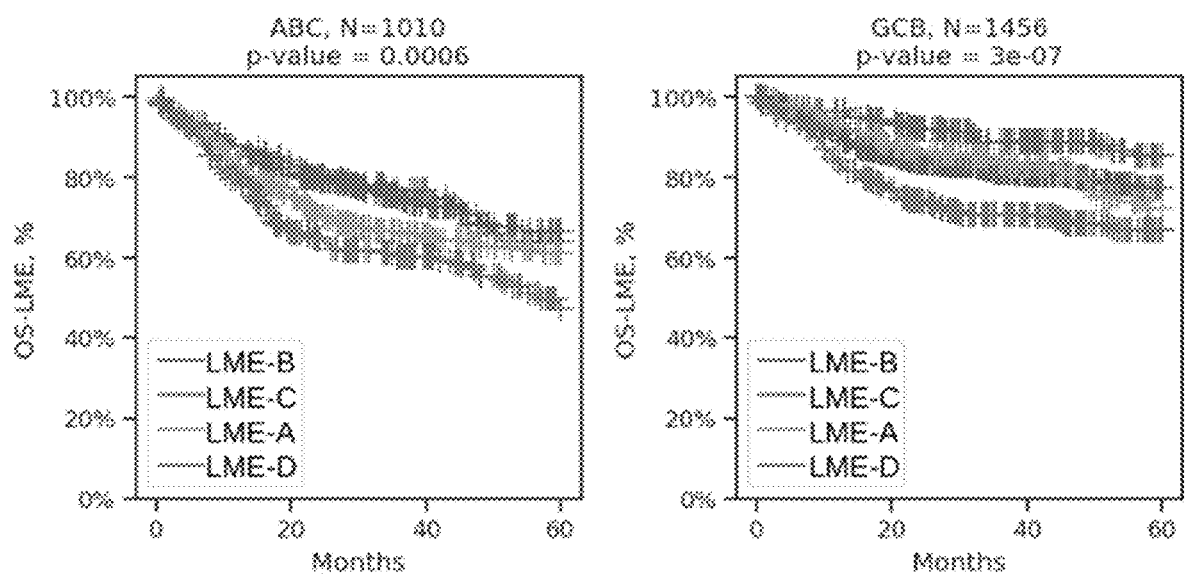
FIG. 3 shows representative data indicating that Lymphoma Microenvironment (LME) types correlate with overall survival (OS), independent of cancer cell of origin (COO), according to certain aspects of the invention. Left panel shows a Kaplan-Meier (KM) survival plot for a sample of 1010 patients having Activated B cell (ABC) lymphoma. Right panel shows a KM survival plot for a sample of 1456 patients having Germinal center B cell-like (GCB) lymphoma.
Figure 4:
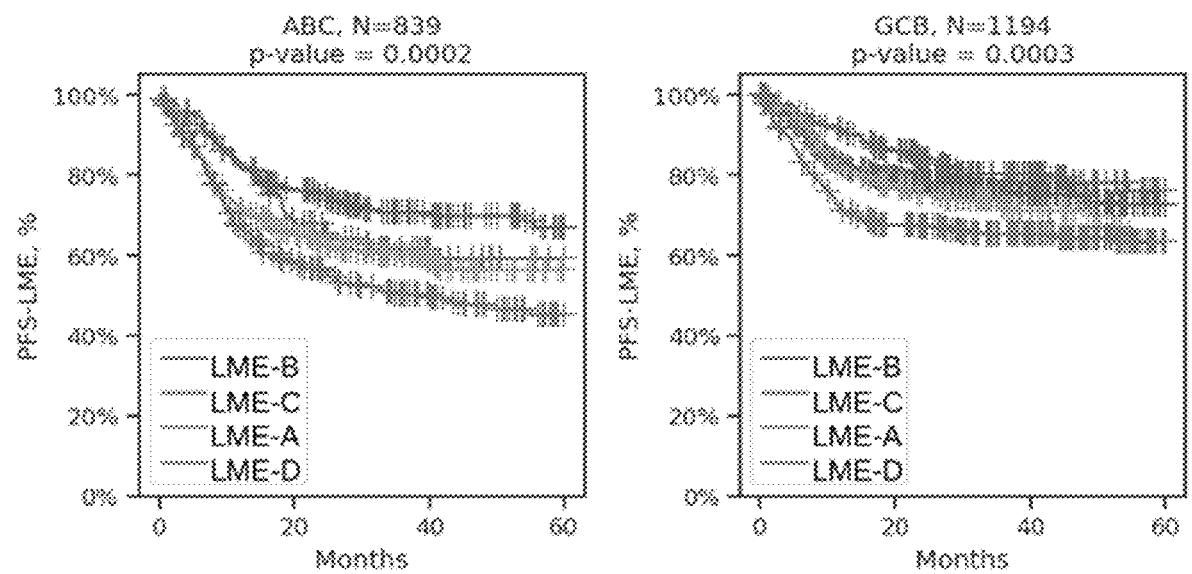
FIG. 4 shows representative data indicating that Lymphoma Microenvironment (LME) types correlate with progression-free survival (PFS), independent of cancer cell of origin (COO), according to certain aspects of the invention. Left panel shows a Kaplan-Meier (KM) survival plot for a cohort of 839 patients having Activated B cell (ABC) lymphoma. Right panel shows a KM survival plot for a cohort of 1194 patients having Germinal center B cell-like (GCB) lymphoma.
Figure 5:
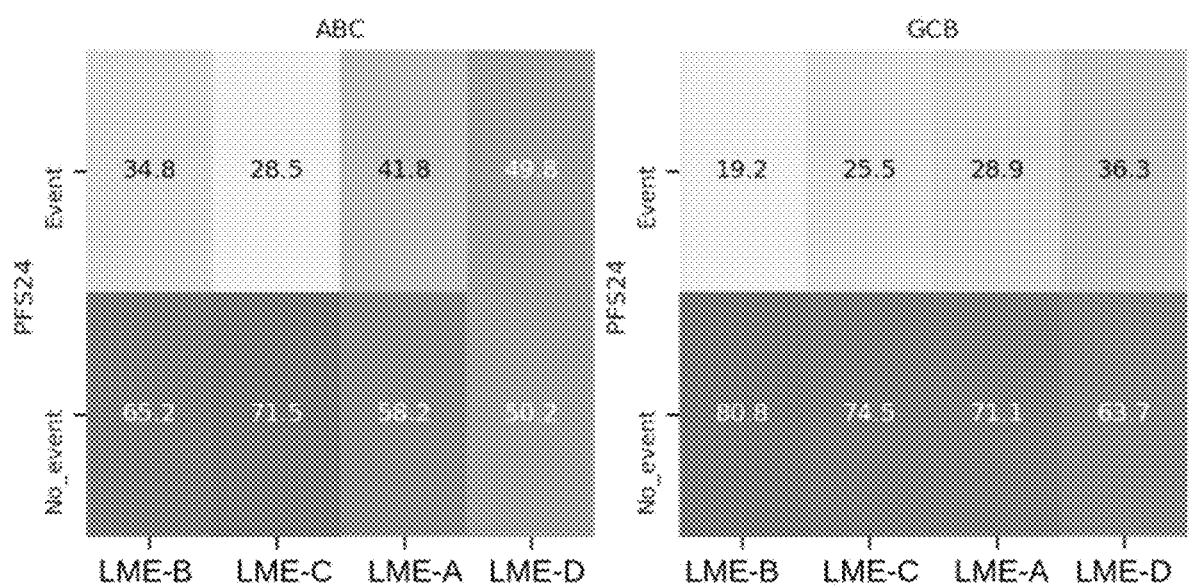
FIG. 5 shows representative data demonstrating stratification of progression-free survival at 24 months (PFS24) according to COO and LME type, according to certain aspects of the invention. The left panel shows stratification of subjects having Activated B cell (ABC) DCBCL and the right panel shows stratification of subjects having Germinal center B cell-like (GCB) DCBCL.

LME types were observed to be associated with OS and progression-free survival at 24 months (PFS24) for each LME type, for each cancel cell of origin (COO) separately. FIG. 3 shows representative data indicating that Lymphoma Microenvironment (LME) types correlate with overall survival (OS), independent of cancer cell of origin (COO), according to certain aspects of the invention. Left panel shows a Kaplan-Meier (KM) survival plot for a sample of 1010 patients having Activated B cell (ABC) lymphoma. Right panel shows a KM survival plot for a sample of 1456 patients having Germinal center B cell-like (GCB) lymphoma. FIG. 4 shows representative data indicating that Lymphoma Microenvironment (LME) types correlate with progression-free survival (PFS), independent of cancer cell of origin (COO), according to certain aspects of the invention. Left panel shows a Kaplan-Meier (KM) survival plot for a cohort of 839 patients having Activated B cell (ABC) lymphoma. Right panel shows a KM survival plot for a cohort of 1194 patients having Germinal center B cell-like (GCB) lymphoma. FIG. 5 shows representative data demonstrating stratification of progression-free survival at 24 months (PFS24) according to COO and TME type, according to certain aspects of the invention. The left panel shows stratification of subjects having ABC and the right panel shows stratification of subjects having GCB.

Figure 6:
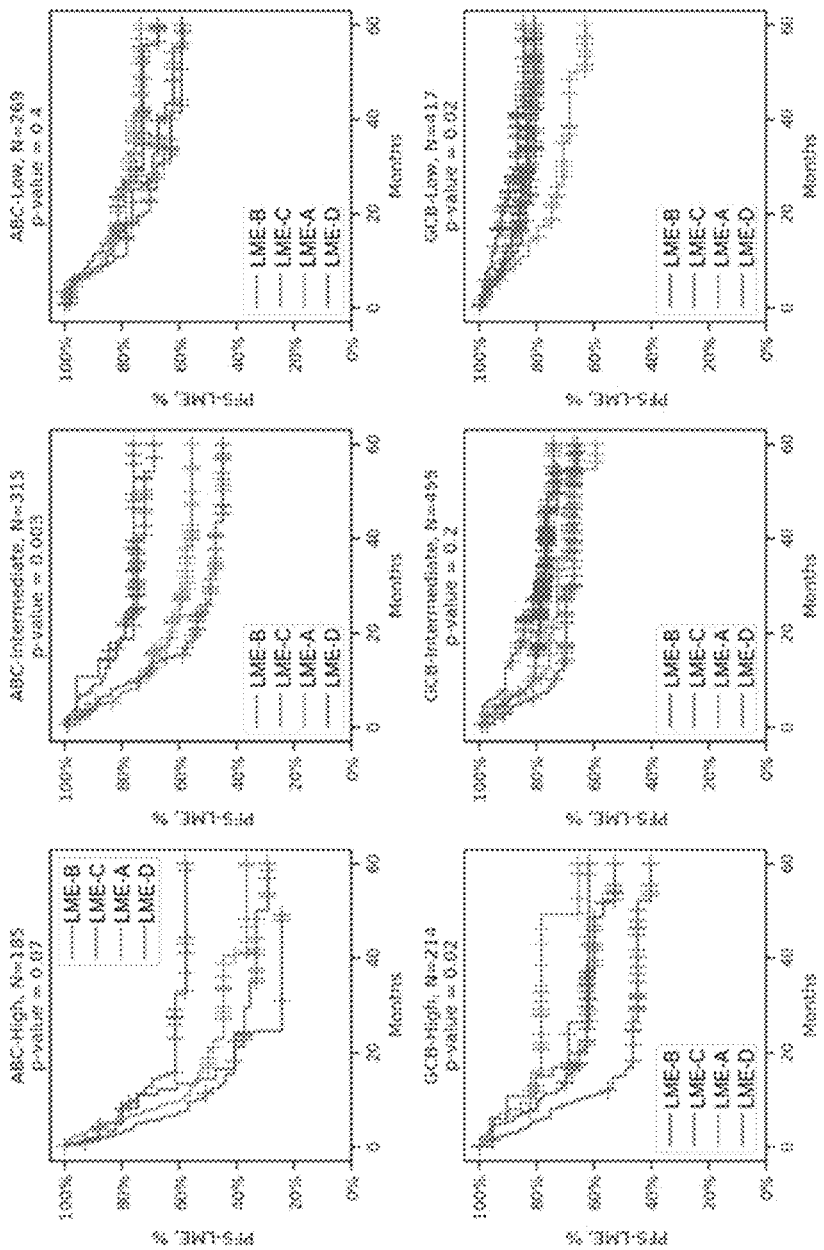
FIG. 6 shows representative data demonstrating stratification of progression-free survival at 24 months (PFS24) according to COO, LME type, and International Prognostic Index (IPI), according to certain aspects of the invention. Data indicate poor prognosis for groups "ABC IPI-High" and (not LME-C, e.g., LME-A, LME-B, or LME-D) or "GCB IPI-High" LME4; ABC IPI-Intermediate LME3/4 subjects also have non-favorable PFS24. As disclosed herein, "ABC IPI-High," "ABC IPI-Intermediate," and "ABC-Low" can be used interchangeably with "ABC High," "ABC Intermediate," and "ABC Low." As disclosed herein, "GCB IPI-High," "GCB IPI-Intermediate," and "GCB-Low" can be used interchangeably with "GCB High," "GCB Intermediate," and "GCB Low."
Figure 6:
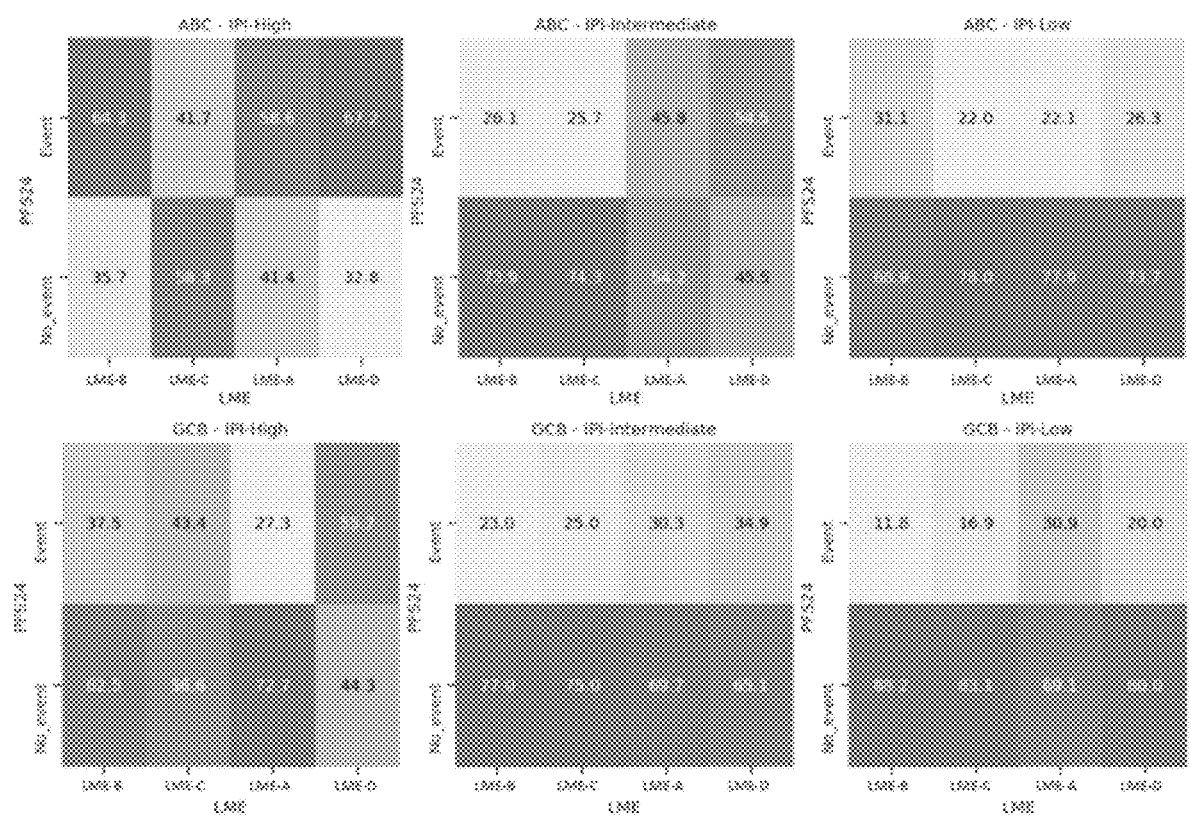

Next, DLBCL samples were typed using LME in combination with COO and International Prognostic Index (IPI) score. Methods of calculating IPI scores are known, for example as described by "International Non-Hodgkin's Lymphoma Prognostic Factors Project. A predictive model for aggressive non-Hodgkin's lymphoma." *N Engl J Med.* 1993; 329(14):987-994. FIG. 6 shows representative data demonstrating stratification of progression-free survival at 24 months (PFS24) according to COO, TME type, and International Prognostic Index (IPI) score, according to certain aspects of the invention. Data indicate poor prognosis for groups "ABC IPI-High" and (not LME-C, e.g., LME-A, LME-B, or LME-D) or "GCB IPI-High" LME4; ABC IPI-Intermediate LME3/4 subject also have non-favorable PFS24.

EQUIVALENTS AND SCOPE

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the technology described herein need not reside on a single computer or processor, but may be distributed in a modular fashion among different computers or processors to implement various aspects of the technology described herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the described methods and systems encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the systems and methods described herein (or aspects thereof) are referred to as comprising particular elements and/or features, certain embodiments of the systems and methods or aspects of the same consist, or consist essentially of, such elements and/or features. For purposes of simplicity, those embodiments have not been specifically set forth in haec verba herein.

It is also noted that the terms "including," "comprising," "having," "containing", "involving", are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the described systems and methods, to the tenth of the unit of the lower limit of the range, unless the context clearly dictates otherwise. The term "consisting" or phrase "consisting of" are intended to be closed terms and do not permit the inclusion of additional elements. Embodiments described as "comprising" an element also contemplate alternative embodiments "consisting of" such an element or elements.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Additionally, as used herein the terms "patient" and "subject" may be used interchangeably. Such terms may include, but are not limited to, human subjects or patients. Such terms may also include non-human primates or other animals.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that fall within the prior art may be explicitly excluded from any one or more of the claims. Because such embodiments are deemed to be known to one of ordinary skill in the art, they may be excluded even if the exclusion is not set forth explicitly herein. Any particular embodiment of the systems and methods described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for determining a Diffuse Large B cell lymphoma (DLBCL) microenvironment (LME) type of a subject, the method comprising:
    using at least one computer hardware processor to perform:
    obtaining at least 5 kb of sequencing data for a subject having, suspected of having, or at risk of having a DLBCL;
    determining a LME signature for the subject using the sequencing data, wherein the sequencing data comprises RNA expression data indicating RNA expression levels of each of the following genes in each of the following gene groups:
        (a) Lymphatic endothelium (LEC): JAM3, PPP1R13B, CXCL12, PDPN, CXADR, FLT4, CCL21, FOXC2, EDNRB, LYVE1, PROX1, SOX18, and JAM2;
        (b) Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2;
        (c) Cancer-associated fibroblasts(CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2;
        (d) Fibroblastic reticular cells (FRC): PDGFRA, ACTA2, ICAM1, NT5E, VIM, PDPN, THY1, DES, VCAM1, PTGS2, and LTBR;
        (e) Matrix (ECM): COL1A1, COL3A1, LGALS7, FN1, VTN, COL1A2, and COL4A1;
        (f) Matrix Remodeling (ECM remodeling): TIMP1, TIMP2, MMP2, MMP9, and CA9;
        (g) Granulocyte traffic: KITLG, CXCL8, CXCR1, CXCR2, CXCL5, KIT, CCL11, CCR3, CXCL1, and CXCL2;
        (h) Protumor cytokines (IS cytokines): CCL4, IL6, TNFSF13B, MIF, CXCL8, IL22, and IL10;
        (i) Follicular Dendritic Cells (FDC): PDPN, TNFRSF1A, LTBR, FDCSP, CLU, PRNP, and BST1;
        (j) Macrophages: IL10, MSR1, ARG1, CSF1R, CD163, MRC1, and CSF1;

(k) M1 signature (activated M1): TNF, NOS2, IL1B, and CMKLR1;
(l) Effector cell traffic (T cell traffic): CXCL11, CXCL10, CXCL9, CXCR3, CX3CL1, CCL5, and CX3CR1;
(m) Major histocompatibility complex II (MHC-II): HLA-DQB1, HLA-DPB1, HLA-DPA1, HLA-DRA, HLA-DQA1, HLA-DMA, HLA-DRB1, and HLA-DMB;
(n) Major histocompatibility complex I (MHC-I): TAP1, HLA-C, B2M, HLA-B, HLA-A, and TAP2;
(o) Follicular B helper T cells (TFH): CD40LG, SH2D1A, CD84, CXCR5, IL4, IL6, MAF, BCL6, IL21, and ICOS;
(p) Regulatory T cells (Treg): CCR8, CTLA4, IKZF2, IKZF4, FOXP3, IL10, and TNFRSF18;
(q) T cells (TIL): CD3D, TRAT1, TBX21, TRBC2, ITK, CD28, CD3E, TRBC1, TRAC, and CD3G;
(r) Checkpoint inhibition (IS checkpoints): CTLA4, HAVCR2, CD274, PDCD1, BTLA, TIGIT, PDCD1LG2, and LAG3;
(s) Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1;
(t) B cell traffic: CXCL13, CXCR5, CCR6, and CCL20;
(u) Benign B cells (B cells): CD79B, MS4A1, STAP1, TNFRSF17, CD24, CD22, TNFRSF13B, BLK, CD19, PAX5, CD79A, TNFRSF13C, and FCRL5; and
(v) Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1, and wherein the LME signature comprises:
(i) a gene expression signature comprising a plurality of gene group expression scores, wherein the gene group expression scores are produced by performing gene set enrichment analysis (GSEA) using the RNA expression levels for each of the following genes in each of the following gene groups:
(a) Lymphatic endothelium (LEC): JAM3, PPP1R13B, CXCL12, PDPN, CXADR, FLT4, CCL21, FOXC2, EDNRB, LYVE1, PROX1, SOX18, and JAM2;
(b) Angiogenesis (VEC): CDH5, PGF, PDGFC, TEK, VEGFC, CXCL8, VWF, CXCR2, ANGPT1, CXCL5, FLT1, VEGFA, KDR, VEGFB, and ANGPT2;
(c) Cancer-associated fibroblasts (CAF): COL1A1, MMP2, LGALS1, MMP7, LRP1, CD248, S100A4, FAP, FGF2, MMP9, CTGF, ACTA2, FN1, COL1A2, COL5A1, COL6A1, MMP3, CA9, PRELP, FBLN1, COL6A3, COL11A1, TGFB3, MMP12, MFAP5, MMP1, COL6A2, TIMP1, COL4A1, TGFB1, LUM, LGALS9, PTGS2, and TGFB2;
(d) Fibroblastic reticular cells (FRC): PDGFRA, ACTA2, ICAM1, NT5E, VIM, PDPN, THY1, DES, VCAM1, PTGS2, and LTBR;
(e) Matrix (ECM): COL1A1, COL3A1, LGALS7, FN1, VTN, COL1A2, and COL4A1;
(f) Matrix Remodeling (ECM remodeling): TIMP1, TIMP2, MMP2, MMP9, and CA9;
(g) Granulocyte traffic: KITLG, CXCL8, CXCR1, CXCR2, CXCL5, KIT, CCL11, CCR3, CXCL1, and CXCL2;
(h) Protumor cytokines (IS cytokines): CCL4, IL6, TNFSF13B, MIF, CXCL8, IL22, and IL10;
(i) Follicular Dendritic Cells (FDC): PDPN, TNFRSF1A, LTBR, FDCSP, CLU, PRNP, and BST1;
(j) Macrophages: IL10, MSR1, ARG1, CSF1R, CD163, MRC1, and CSF1;
(k) M1 signature (activated M1): TNF, NOS2, IL1B, and CMKLR1;
(l) Effector cell traffic (T cell traffic): CXCL11, CXCL10, CXCL9, CXCR3, CX3CL1, CCL5, and CX3CR1;
(m) Major histocompatibility complex II (MHC-II): HLA-DQB1, HLA-DPB1, HLA-DPA1, HLA-DRA, HLA-DQA1, HLA-DMA, HLA-DRB1, and HLA-DMB;
(n) Major histocompatibility complex I (MHC-I): TAP1, HLA-C, B2M, HLA-B, HLA-A, and TAP2;
(o) Follicular B helper T cells (TFH): CD40LG, SH2D1A, CD84, CXCR5, IL4, IL6, MAF, BCL6, IL21, and ICOS;
(p) Regulatory T cells (Treg): CCR8, CTLA4, IKZF2, IKZF4, FOXP3, IL10, and TNFRSF18;
(q) T cells (TIL): CD3D, TRAT1, TBX21, TRBC2, ITK, CD28, CD3E, TRBC1, TRAC, and CD3G;
(r) Checkpoint inhibition (IS checkpoints): CTLA4, HAVCR2, CD274, PDCD1, BTLA, TIGIT, PDCDILG2, and LAG3;
(s) Natural Killer Cells (NK cells): SH2D1B, GZMH, GZMB, CD160, KLRK1, NCR3, CD244, IFNG, GNLY, NCR1, CD226, NKG7, EOMES, KLRC2, FGFBP2, KIR2DL4, and KLRF1;
(t) B cell traffic: CXCL13, CXCR5, CCR6, and CCL20;
(u) Benign B cells (B cells): CD79B, MS4A1, STAP1, TNFRSF17, CD24, CD22, TNFRSF13B, BLK, CD19, PAX5, CD79A, TNFRSF13C, and FCRL5; and
(v) Tumor proliferation rate (cell proliferation): MCM6, AURKB, ESCO2, CCNB1, AURKA, MKI67, CCND1, CCNE1, MCM2, MYBL2, E2F1, CETN3, CDK2, PLK1, and BUB1; and
(ii) one or more PROGENY pathway scores for the sequencing data, wherein the one or more PROGENY pathway scores are selected from Nuclear factor kappa B (NFkB), Phosphoinositide 3-kinase (PI3K), and p53; and assigning, from a plurality of LME types comprising LME-A type, LME-B type, LME-C type, and LME-D type, an LME type D (LME-D) to the subject using the LME signature, wherein the LME type D subject comprises lymphoma cells having hypermethylation and activation of PI3K signaling: wherein the assigning comprises associating the LME signature of the subject with a cluster of previously determined LME signatures selected from a LME-A type cluster, LME-B type cluster, LME-C type cluster, and LME-D type cluster; and administering a CAR-T therapy to the subject assigned as having an LME-D type.

2. The method of claim 1, further comprising identifying the subject as having an increased chance of a PFS24 event relative to other LME types when the subject is assigned type LME-D.

3. The method of claim 1, wherein the method further comprises obtaining an International Prognostic Index (IPI) score of the subject, wherein the IPI score is Low, Intermediate, or High.

4. The method of claim 1, further comprising: (i) identifying the subject as having an increased chance of a PFS24 event relative to . . . event relative to other LME types when the DLBCL is type LME-D GCB and the IPI score is High; or (ii) identifying the subject as having an increased chance of a PFS24 event (e.g., relapse, retreatment, or death) relative to other LME types when the DLBCL is type LME-D ABC and the IPI score is Intermediate.

* * * * *

UNITED STATES PATENT AND TRADEMARK OFFICE
CERTIFICATE OF CORRECTION

| | |
|---|---|
| PATENT NO. | : 11,568,959 B2 |
| APPLICATION NO. | : 17/368674 |
| DATED | : January 31, 2023 |
| INVENTOR(S) | : Nikita Kotlov et al. |

It is certified that error appears in the above-identified patent and that said Letters Patent is hereby corrected as shown below:

In the Claims

Column 67, Claim 4, Line 7:
"event relative to ...event relative to other LME types when"

Should read:
--event relative to other LME types when--

Column 67, Claim 4, Line 11:
"of a PFS24 event (e.g., relapse, retreatment, or death)"

Should read:
--of a PFS24 event--

Signed and Sealed this
Twenty-eighth Day of March, 2023

Katherine Kelly Vidal
*Director of the United States Patent and Trademark Office*